(12) United States Patent
Tendler et al.

(10) Patent No.: US 7,534,437 B2
(45) Date of Patent: May 19, 2009

(54) HELMINTH-DERIVED ANTIGENS HAVING CAPACITY OF PROVIDING PROTECTION AGAINST PARASITES

(75) Inventors: Miriam Tendler, Rio de Janeiro (BR);
Naftale Katz, Rio de Janeiro (BR);
Andrew J. Simpson, Rio de Janeiro (BR); Isaias Raw, Sao Paulo (BR);
Paulo Lee Ho, Sao Paulo (BR); Celso Raul Romero Ramos, Sao Paulo (BR)

(73) Assignee: Fundacao Oswaldo Cruz - Fiocruz, Rio de Janeiro (BR)

( * ) Notice: Subject to any disclaimer, the term of this patent is extended or adjusted under 35 U.S.C. 154(b) by 0 days.

(21) Appl. No.: 10/544,035

(22) PCT Filed: Jan. 30, 2004

(86) PCT No.: PCT/BR2004/000005

§ 371 (c)(1),
(2), (4) Date: Sep. 29, 2006

(87) PCT Pub. No.: WO2004/067698

PCT Pub. Date: Aug. 12, 2004

(65) Prior Publication Data

US 2007/0021332 A1  Jan. 25, 2007

(30) Foreign Application Priority Data

Jan. 31, 2003 (BR) .................................... 0303266

(51) Int. Cl.
*A61K 39/00* (2006.01)
*A61K 49/00* (2006.01)
*A61K 39/38* (2006.01)
*A61K 39/02* (2006.01)

(52) U.S. Cl. ...................... 424/185.1; 424/9.1; 424/9.2; 424/184.1; 424/190.1; 424/265.1

(58) Field of Classification Search ................. 424/9.1, 424/9.2, 184.1, 185.1, 190.1, 265.1
See application file for complete search history.

(56) References Cited

U.S. PATENT DOCUMENTS 5,730,984 A * 3/1998 Tendler et al. ............ 424/191.1

* cited by examiner

*Primary Examiner*—Rodney P. Swartz
(74) *Attorney, Agent, or Firm*—Caesar, Rivise, Bernstein, Cohen & Pokotilow, Ltd.

(57) ABSTRACT

The primary objective of the present invention is the development of new mutant forms of the Sm14 protein, for producing a greater production volume. The recombinant proteins here obtained were capable of providing protection against *schistosome* and *fasciola* infection. The level of protection of Sm14 recombinant proteins obtained in the present invention was similar to that reached in the parasite saline extract. The mutant proteins of the present invention have reached approximately 100% of renaturation after the heating at 80° C., different from wild forms of the Sm14 protein. Moreover, after storage for 2 months at 4° C., mutant proteins have shown smaller β-structure loss than wild forms that have shown formation with random structure, as demonstrated by the circular dichroism analysis, indicating the success of mutations.

6 Claims, 18 Drawing Sheets pRSETA-Sm14 (SEQ ID NO: 8)

```
              6xHis-tag                              T7-tag
ATGCGGGGTTCTCATCATCATCATCATCATGGTATGGCTAGCATGACTGGTGGACAGCAA
 M  R  G  S  H  H  H  H  H  H  G  M  A  S  M  T  G  G  Q  Q
                                          BamH I      Sm14 ORF
ATGGGTCGGGATCTGTACGACGATGACGATAAGGATCGATGGGGATCCGTCATGTCTAGT...
 M  G  R  D  L  Y  D  D  D  D  K  D  R  W  G  S  V  M  S  S
              Cleavage site of Enterokinase
``` pET3-His-Sm14, pRSETA-6xHis-Sm14 (SEQ ID NO: 9)

```
         6xHis-tag              BamH I        Sm14 ORF
ATGCATCACCATCACCATCACCTCGAGGGATCCGTCATGTCTAGTTTCTTGGGAAAG...
 M  H  H  H  H  H  H  L  E  G  S  V  M  S  S  F  L  G  K
```

Fig 2B

SEQUENCE LISTING

<160> NUMBER OF SEQ ID NOS: 5

<210> SEQ ID NO 1
<211> LENGTH: 133
<212> TYPE: PRT
<213> ORGANISM: Fasciola hepatica

<400> SEQUENCE: 1

```
Met Ser Ser Phe Leu Gly Lys Trp Lys Leu Ser Glu Ser His Asn Phe
1               5                   10                  15

Asp Ala Val Met Ser Lys Leu Gly Val Ser Trp Ala Thr Ala Gln Ile
                20                  25                  30

Gly Asn Thr Val Thr Pro Thr Val Thr Phe Thr Met Asp Gly Asp Lys
                35                  40                  45

Met Thr Met Leu Thr Glu Ser Thr Phe Lys Asn Leu Ser Cys Thr Phe
        50                  55                  60

Lys Phe Gly Glu Glu Phe Asp Glu Lys Thr Ser Asp Gly Ala Asn Val
65                  70                  75                  80

Lys Ser Val Val Glu Lys Asn Ser Glu Ser Lys Leu Thr Gln Thr Gln
                85                  90                  95

Val Asp Pro Lys Asn Thr Thr Val Ile Val Ala Glu Val Asp Gly Asp
                100                 105                 110

Thr Met Lys Thr Thr Val Thr Val Gly Asp Val Thr Ala Ile Ala Asn
        115                 120                 125

Tyr Lys Ala Leu Ser
    130
```

<210> SEQ ID NO 2
<211> LENGTH: 133
<212> TYPE: PRT
<213> ORGANISM: Fasciola hepatica

```
<400> SEQUENCE: 2

Met Ser Ser Phe Leu Gly Lys Trp Lys Leu Ser Glu Ser His Asn Phe
1               5                   10                  15

Asp Ala Val Ser Ser Lys Leu Gly Val Ser Trp Ala Thr Arg Gln Ile
            20                  25                  30

Gly Asn Thr Val Thr Pro Thr Val Thr Phe Thr Met Asp Gly Asp Lys
            35                  40                  45

Met Thr Met Leu Thr Glu Ser Thr Phe Lys Asn Leu Ser Cys Thr Phe
    50                  55                  60

Lys Phe Gly Glu Glu Phe Asp Glu Lys Thr Ser Asp Gly Arg Asn Val
65              70                  75                  80

Lys Ser Val Val Glu Lys Asn Ser Glu Ser Lys Leu Thr Gln Thr Gln
                85                  90                  95

Val Asp Pro Lys Asn Thr Thr Val Ile Val Arg Glu Val Asp Gly Asp
            100                 105                 110

Thr Met Lys Thr Thr Val Thr Val Gly Asp Val Thr Ala Ile Arg Asn
            115                 120                 125

Tyr Lys Arg Leu Ser
        130

<210> SEQ ID NO 3
<211> LENGTH: 133
<212> TYPE: PRT
<213> ORGANISM: Fasciola hepatica

<400> SEQUENCE: 3

Met Ser Ser Phe Leu Gly Lys Trp Lys Leu Ser Glu Ser His Asn Phe
1               5                   10                  15

Asp Ala Val Val Ser Lys Leu Gly Val Ser Trp Ala Thr Arg Gln Ile
            20                  25                  30

Gly Asn Thr Val Thr Pro Thr Val Thr Phe Thr Met Asp Gly Asp Lys
            35                  40                  45

Met Thr Met Leu Thr Glu Ser Thr Phe Lys Asn Leu Ser Cys Thr Phe
    50                  55                  60

Lys Phe Gly Glu Glu Phe Asp Glu Lys Thr Ser Asp Gly Arg Asn Val
65              70                  75                  80

Lys Ser Val Val Glu Lys Asn Ser Glu Ser Lys Leu Thr Gln Thr Gln
                85                  90                  95

Val Asp Pro Lys Asn Thr Thr Val Ile Val Arg Glu Val Asp Gly Asp
            100                 105                 110

Thr Met Lys Thr Thr Val Thr Val Gly Asp Val Thr Ala Ile Arg Asn
            115                 120                 125

Tyr Lys Arg Leu Ser
        130

<210> SEQ ID NO 4
<211> LENGTH: 133
<212> TYPE: PRT
<213> ORGANISM: Fasciola hepatica

<400> SEQUENCE: 4

Met Ser Ser Phe Leu Gly Lys Trp Lys Leu Ser Glu Ser His Asn Phe
1               5                   10                  15

Asp Ala Val Ala Ser Lys Leu Gly Val Ser Trp Ala Thr Arg Gln Ile
            20                  25                  30
```

```
Gly Asn Thr Val Thr Pro Thr Val Thr Phe Thr Met Asp Gly Asp Lys
            35                  40                  45

Met Thr Met Leu Thr Glu Ser Thr Phe Lys Asn Leu Ser Cys Thr Phe
        50                  55                  60

Lys Phe Gly Glu Glu Phe Asp Glu Lys Thr Ser Asp Gly Arg Asn Val
65                      70                  75                  80

Lys Ser Val Val Glu Lys Asn Ser Glu Ser Lys Leu Thr Gln Thr Gln
                85                  90                  95

Val Asp Pro Lys Asn Thr Thr Val Ile Val Arg Glu Val Asp Gly Asp
            100                 105                 110

Thr Met Lys Thr Thr Val Thr Val Gly Asp Val Thr Ala Ile Arg Asn
            115                 120                 125

Tyr Lys Arg Leu Ser
        130

<210> SEQ ID NO 5
<211> LENGTH: 133
<212> TYPE: PRT
<213> ORGANISM: Fasciola hepatica

<400> SEQUENCE: 5

Met Ser Ser Phe Leu Gly Lys Trp Lys Leu Ser Glu Ser His Asn Phe
1               5                   10                  15

Asp Ala Val Thr Ser Lys Leu Gly Val Ser Trp Ala Thr Arg Gln Ile
            20                  25                  30

Gly Asn Thr Val Thr Pro Thr Val Thr Phe Thr Met Asp Gly Asp Lys
            35                  40                  45

Met Thr Met Leu Thr Glu Ser Thr Phe Lys Asn Leu Ser Cys Thr Phe
        50                  55                  60

Lys Phe Gly Glu Glu Phe Asp Glu Lys Thr Ser Asp Gly Arg Asn Val
65                      70                  75                  80

Lys Ser Val Val Glu Lys Asn Ser Glu Ser Lys Leu Thr Gln Thr Gln
                85                  90                  95

Val Asp Pro Lys Asn Thr Thr Val Ile Val Arg Glu Val Asp Gly Asp
            100                 105                 110

Thr Met Lys Thr Thr Val Thr Val Gly Asp Val Thr Ala Ile Arg Asn
            115                 120                 125

Tyr Lys Arg Leu Ser
        130
```

HELMINTH-DERIVED ANTIGENS HAVING CAPACITY OF PROVIDING PROTECTION AGAINST PARASITES

TECHNICAL FIELD

The present invention, on its more general aspect, relates to antigenic helminth-derived material that is capable of providing protection against parasites.

The invention also relates to vaccines providing a protecting immunity against helminth infection.

The invention is also related to a system of mammal-host vaccination against helminth infections.

BACKGROUND OF THE INVENTION

Among helminths, digenetic trematodes comprise more than 100 families. Most trematodes are relatively little aggressive parasites living in intestines and other organs of vertebrates; thus, they have been receiving little attention from parasitologists that make use of applied parasitology. Trematodes known by causing serious diseases to humans, i.e. blood stream trematodes, *Schistosoma*, as well as liver and lung trematodes are very important animal-infecting parasites.

Schistosomiasis is a disease caused by blood trematodes belonging to family Schistosomatideae, class Trematoda, subclass Diginea, and gender *Schistosoma*. Humans are mainly parasitized by three parasite species of the gender *Schistosoma*: *S. mansoni* (found in Africa and South America), *S. haematobium* (Africa and Middle East), and *S. japonicum* (Asia). Adult worms of *S. mansoni* and *S. japonicum* are located in mesenteric veins of intestines, while S. *haematobium* occurs in veins surrounding the bladder.

*Fasciola*, the most important liver trematode, is the predominant parasite in domestic ruminants and it is responsible for serious economical losses over the world, reaching the bovine, caprine, and ovine cattle.

The main disease characteristic, responsible for the pathology, morbidity and mortality of the cited animals, is based on the host's hepatic tissue destruction, as a result of the damages caused to bile ducts, where the adult specimen *Fasciola* lives. Young animals, particularly infected by *Fasciola hepatica*, have higher morbidity and consequently they die. *Fasciola*, some times, can also parasitize humans, when an opportunity of it enters in contact with the habitat of the animal disease occurs. This fact is more frequent in Cuba and some countries of Latin America. However, the real human's liver trematode is another parasite called *Clonorchis sinensis*, which is pervasive in China, Japan, Korea, Vietnam, and India.

Basically, the pathology is caused by the thickening of the bile duct walls and, in more severe cases, may cause liver cirrhosis and death.

Both *Fasciola* and *Clonorchis* enter passively into the host, under a larval form called metacercaria that is ingested with food (pasture and raw fish for *Fasciola* and *Clonorchis*, respectively); however, their pathway of migration into vertebrate host organism occurs through bile ducts and they differ amongst themselves. While *Clonorchis* reaches the bile tree through intestines, and ampulla of Vater; *Fasciola* migrates through abdominal cavity, penetrating actively into the liver wall, by its capsule, reaching the parenchyma and the bile system; thus, causing serious damages to host's tissues.

Regarding the fascioliasis in pets, there are conflicting results and little evidence suggesting that sheep or goats acquire immunity against *Fasciola hepatica* (Sinclair, 1967) after immunization with raw extracts.

There is evidence showing that the infection may persist for at least 11 years in sheep experimentally infected (Durbin, 1952). It was also reported very little or no reaction of the host to parasite; thus, the infected sheep survival will depend entirely on the number of metacercaria ingested (Boray, 1969). The bovine cattle are known to be more resistant against *F. hepatica*. *Fasciola* in these cases usually lives in host for an average of 9-12 months; however, young animals are the most clinically affected by fascioliasis.

In order to identify the antigens that can be used for immunoprophylaxis and that could serve as a basis for developing vaccines effective against fascioliasis, several attempts have been made. Several scientists have been following basically two independent experimental strategies based on: 1) immunity induced by irradiated living cercaria, the basis of the considered living vaccine and, 2) immunity induced by the called non-living vaccines.

However, few works have been published in the context of obtaining acquired resistance to *Fasciola hepatica* in calves by using somatic raw extracts from the adult parasite. Ross, 1967, Hall and Lang, 1978, Hillyer, 1979 have reported conflicting data in this context.

The immunity induced by vaccines obtained from irradiation of metacercaria, i.e. irradiated or attenuated living or non-living vaccines, also has lead to frustrating results in experiments performed with mice, rabbits and sheep (Campbell et al, 1978, Hughes, 1963), since no evidence of the development of important immunity has occurred after the irradiated metacercaria administration in these animals.

Additionally, experiments with distinct extracts from excretion and secretion products of trematodes, in their adult form, obtained directly from bile ducts, have been shown to be non-immunogenic since the animals vaccinated with materials originating from these parasitic forms, similarly to controls of the experiments, presented very low or no protection and lesions, from the pathological point of view, in the liver parenchyma.

It is expected, on the state-of-the-art basis, that the bovine cattle can respond better to vaccination with non-living vaccines. For the caprine cattle, there are no experimental indications suggesting that similar situation could be anticipated based on merely mediocre protection induced by the administration of a series of distinct antigens in experiments with these animals.

Campbell et al (1977) has focused the induction of protecting immunity by heterologous immunity. The study of this perspective showed that the infection of sheep by *Cysticercus tenuicollis*, the metacestode step of the measle (*Taenia hydatigena*) in dogs, produces partial protection against *Fasciola hepatica*. However, Hughes et al (1978) did not confirm this result. In other experiments, also was observed the incapacity of inducing protection with this cestode against *Fasciola hepatica* in experimental animals.

Adult and bisexual *S. mansoni*-infected mice developed a statistically significant resistance to *Fasciola hepatica* as well as against concomitant infections by both parasites resulting in a decreased amount of subsequent parasitic load and also a decreased number of eggs per adult worm (Christensen et al, 1978). The *S. bovis*-infected calves also showed some resistance to *Fasciola hepatica* and less marked liver damage (Sirag et al, 1981).

Pelley and Hillyer, 1978 & Hillyer and de Atica, 1980, have reported common antigens to *Fasciola hepatica* and *Schistosoma mansoni* found in *Schistosoma* eggs. The occurrence of false-positive reactions, in areas where both parasites are endemic, is another finding indicating cross reactivity and immunity. Hillyer, 1985 (Hillyer, G. V. 1985 "Induction of immunity in mice to *Fasciola hepatica* with *Fasciola/Schistosoma* cross-reactive defined immunity antigen". Am. J. Trop. Med. Hyg. 34(6), pp. 1127-1131) and Hillyer et al, 1987 (Hillyer, G. V., Haroun, E. T. M., Hernandez, A. and Soler of Galanes, M. 1987. "Acquired resistance to *F. hepatica* in cattle using a purified adult worm antigen". Am. J. Trop. med. Hyg. 37(2). pp. 363-369) have also demonstrated that an antigenic mixture derived from *Fasciola hepatica* can provide protection against subsequent infections caused by *Fasciola hepatica* and *Schistosoma mansoni*.

Thus, it is believed, an effective vaccine will be the most powerful method, with a better cost/benefit relation, stopping the disease transmission and eradicating it from the human context regarding schistosomiasis; and from the veterinary context regarding fascioliasis.

A number of host species may develop partial resistance to *Schistosoma mansoni* starting from the initial infection or immunization with irradiated cercaria (Smithers, S. R. and Doenhoff, M. 1982. "Schistosomiasis" In: Immunology of Parasitic Infections. Blackwell Scientific Publications, 2nd Edition, Chapter 17, pp. 527-607). The state-of-the-art information, regarding the possibility of performing the immunization using raw extracts or material originating from *Schistosoma mansoni* parasitic forms (Clegg & Smith, 1978), has been making possible to produce a defined and effective vaccine against the parasite by using parasite antigens, i.e. non-living vaccines (Tendler, M. 1987. "*S. mansoni*: Protective antigens". Mem. Inst. Oswaldo Cruz. Vol. 82. Suppl. IV. pp. 125-128). However, for most of the experiments using chemically defined and purified material, the greatest limitation was the incomplete degree of protection obtained in animals. As described by several authors and reviewed by Smithers, in 1982 (Smithers, S. R. 1982. "Fascioliasis and other Trematode Infections". In: Immunology of Parasitic Infections. Blackwell Scientific Publications 2nd Edition, Chapter 17, pp. 608-621) there was already a consensus about the necessity for increasing the protection level induced in the experience-based immunoprophylaxis. However, it has been very difficult to settle a good animal model for the development of an effective schistosomiasis vaccine. The progress towards this target depends on the identification and refinement of highly effective antigenic molecules that could mediate the protecting immunity. (Tendler, M. "*Schistosoma mansoni*: Protective Antigens", Mem. do Inst. Oswaldo Cruz. Rio de Janeiro, Vol. 82, Suppl. IV: 125-128, 1987).

In previous studies for finding antigens that mediate the schistosome-protecting immunity, the use of a complex mixture (called SE) of *Schistosoma* components early released by incubating adult living worms in buffered salt solution (Tendler, M. & Scarpin, M. 1979. "The presence of *S. mansoni* antigens in solutions used for storing adult worms". Rev. Inst. Med. Trop. 21(6), pp. 293-296; Kohn et al, 1979). For the purpose of obtaining protection against cercaria infection through a vaccine, an experimental model was observed in two non-syngeneic animal hosts, with distinct susceptibilities to *S. mansoni* infection. One of them, the mouse, being susceptible and the other, the rabbit, partially resistant to infection.

It was possible to establish, in *S. mansoni* model of New Zealander rabbit, a reliable standard of percutaneous infection, with the recovery of homogeneous parasitic loads in number and size of parasites and the male/female ratio, during long term after the infection (Tendler, M., Lima, A., Pinto, R., Cruz, M., Brascher, H., Katz, N. 1982 "Immunogenic and protective activity of an extract of *S. mansoni*". Mem. Inst. Oswaldo Cruz. Rio de Janeiro. Vol. 77(3), pp. 275-283; Tendler, M. 1985 and Tendler, M. 1986). Recent data suggest that the rabbit used as an experimental *S. mansoni* host may represent a new disease-immunity model.

Immunization experiments performed with rabbits using the mixture SE have resulted in very high protection levels after the challenge infection (Scarpin, M., Tendler, M. Messineo, L., Katz, N. 1980 "preliminary studies with a *Schistosoma mansoni* saline extract inducing protection in rabbits against the challenge infection". Rev. Inst. Med. Trop. Sao Paulo. 22(4), pp. 164-172; Tendler, M. 1980; Tendler, M. 1982) (90% reduction in the average parasitic load of vaccinated animals compared to sex- and age-matched control animals infected with the same cercaria batch obtained from strain LE, a Brazilian *S. mansoni* strain). Besides presenting total protection against lethal infections, the SW (Swiss Webster) mice SE-immunized mice also showed significant protection when challenged with cercaria (Tendler, 1986). In order to assess the resistance, the vaccinated and challenged animals together with their respective controls, are subjected to venous perfusion of porta-hepatis and mesenteric systems for recovering and counting the adult parasitic load. The protection degree is calculated by the difference between the number of parasites recovered from controls compared to vaccinated animals (Tendler et al, 1982).

Based on "in vitro" evidence on the effectiveness of antibodies against distinct evolutionary parasite phases, in assays of eosinophilic or complement-dependent cytotoxicity (Grzych et al, 1982; Smith et al, 1982), the characterization of antigens recognized by the serum of knowingly resistant animals is used for identifying antigenic molecules potentially capable to mediate the protecting immunity (Bickle et al, 1986; Horowitz & Amon, 1985). Western blot experiments were performed to analyze the response from antibodies in SE-vaccinated rabbits. Testing the SE antigens against a panel of antisera of rabbits immunized with the same scheme (SE-CFA—Complex Mixture of the Components of the Complete Freund's *Schistosoma*-Adjuvant) the authors were capable to demonstrate, in immunoblots, the occurrence of two patterns of recognition of SE components.

Interestingly, the sera of rabbits that developed total protection only recognized some SE components. This result made possible to authors identify two SE-components groups: one group common to all individuals and other antigenic group only recognized by the serum of SE-vaccinated animals (rabbits) that were totally protected. These two recognition patterns were named pattern of "High" or "Low" protection and were used as "differential" antibodies. Based on both patterns of SE-component recognition by polyclonal sera of rabbits with different response to the same immunization scheme (probably due to the individual pattern of variation expected in non-syngeneic populations), a strategy for screening cDNA libraries in both sera was used. Taking into account the limitation of the incomplete knowledge about critical mechanisms of protecting response, both in experimental animals and in clinical schistosomiasis, the frequently adopted screening procedures comprise the use of either human sera from immune or susceptible subjects potentially infected (Carter & Colley, 1986) or monoclonal and polyclonal antibodies from immunized animals directed against several non-characterized antigens (Lanar et al, 1986; Balloul et al, 1987).

In initial attempts of molecular cloning of potential SE-protecting components, using differential screening, Drs. Klinkert, University of Heidelberg and Donnelson/Henkle, Iowa University, respectively, built two cDNA libraries of adult *S. mansoni* and *S. japonicum* worms. We can drawn a parallel from the immunoblot results, in which two distinct groups of clones were selected, corresponding potentially to the differential pattern of recognition of anti-SE rabbit sera with high and low protection. Parallel experiments, whose objective was to identify SE components, immunoblots of polyclonal rabbit anti-SE (high and low protection) sera were compared to rabbit sera, against purified *Schistosoma* paramiosine (provided by Dr. A. Sher, NIH). This protein had been defined as a molecule showing partial protection against *Schistosoma mansoni* infection of syngeneic mice (Lanar et al, 1986), its molecular weight is $Mr(\times10^{-3})$ 97, and it is sensitive to proteolytic degradation, resulting in two by-products of $Mr(\times10^{-3})$ 95 and 78 (Pearce et al, 1986).

The complex 97/95/78 was recognized by anti-SE sera with low and high protection and by monospecific serum against paramiosine. Besides the paramiosine, the high-protection, anti-SE sera have also recognized other peptides and proteins to be characterized and tested for their protection and immunological function.

The paramiosine detection, as a SE component, reinforces previous data from indirect immunofluorescence assays performed on section from adult *Schistosoma* worms, with rabbit's anti-SE serum, that reacted with the parasite surface and with the area among muscular layers (Mendonça et al, 1987), similarly to the demonstrated for the paramiosine (Pearce et al, 1986).

The result above was also concordant with the results from the screening of cDNA libraries performed as mentioned. Again the common paramiosine clones were isolated with anti-paramiosine and anti-SE sera. Clones recognized only by rabbit's anti-SE sera (high protection) were also obtained.

Among the other SE components having lower molecular weight, the 31/32-kDa component, described as potential candidate for schistosomiasis diagnosis, was also identified (Klinkert et al, 1987) and recently reported as a protease located in digestive tube, (Klinkert et al, 1988). These and other antigens identified in SE have shown to induce very low protection in vaccination testing.

For obtaining early released antigens from adult living worms (especially from secretion/excretion and tegument components), an incubation of adult living worms newly perfused in a chemically defined medium (PBS-Phosphate Buffered Saline), was used.

This strategy was adopted based on previous and frustrated attempts of other authors, aiming the induction of high resistance against *Schistosoma* infection from distinct raw *S. mansoni* extracts that could be theoretically depleted from relevant functional antigens. This premise was influenced mainly because the antigenic extraction procedures, commonly adopted by other authors, have used non-living parasites. Indeed, by using SE emulsified in CFA (Complete Freund's Adjuvant, as preferential adjuvant), administered by intradermal/subcutaneous route, high and long-term protection is reached in two experimental animal models against *S. mansoni* infection. The reason for using a rabbit model, that is uncommon in protection assays, was to reach an initial identification of potentially protecting antigens in partially resistant hosts (to be later tested in susceptible hosts) that, however, would be able to amplify the immune response and the effective mechanisms of parasitic death, once the rabbits are known as potent producer of antibodies.

Studies on immune response induced in vaccinated animals, aiming to identify functional, and relevant SE-protecting components, parasitic death site and mechanisms, as well as protection markers were the focus of our efforts in the last years. However, just recently, the information about SE composition, by using the identification and separation of their protecting components, became available.

The U.S. Pat. No. 4,396,000, published on Aug. 2, 1983, on behalf of Luigi Messineo & Mauro Scarpin (according to Reexamination Certificate 461 B1 U.S. Pat. No. 4,396,000 published on Feb. 11, 1986, the patent was revoked), describes an extract of adult *Schistosoma mansoni* worms, obtained by incubation in buffered sodium phosphate—sodium chloride—PBS 0.15 M (pH=5.8), comprising proteins, carbohydrates, and nucleic acids and/or by-products from these nucleic acids, separated in 4 main fractions by Sephadex G-100 and G-200 gel column chromatography. Immunodiffusion tests using rabbit whole anti-extract serum have shown 3 precipitation lines corresponding to fractions I and II and 1 to fractions III and IV. The rabbits immunized with the whole extract have developed total or partial resistance (at least 77%) against the subsequent challenge infection. The saline extract's antigenic material showed to be an effective vaccine in the treatment and immunization of schistosomiasis and other *Schistosoma* infections.

Illustratively, we emphasize that the U.S. Pat. No. 4,396,000 was revoked based on published articles. Among the data set corresponding to the antecedents of the present invention, we have the cloning and sequencing of a SE-derived component identified as being Sm14.

Moser et al (Moser, D., Tendler, M., Griffiths, G. and Klinkert, M. Q., have a published study "A 14 kDa *Schistosoma mansoni* Polypeptide is Homologous to a gene family of Fatty Acid Binding Proteins" Journal of Biological Chemistry vol. 266, No. 13, pp. 8447-8454, 1991). This study describes the gene sequencing and demonstrates the functional activity of the Sm14 as a fatty acid binding protein.

A complete nucleotide sequence that codifies the *Schistosoma mansoni* protein, Sm14, was obtained and determined from cDNA clones propagated in bacteriophage λgt 11 in *Escherichia coli*. The 14.8-kDa protein presents significant similarity, indicating homology, with a family of related polypeptide linked with hydrophobic ligands. Based on their affinity with long-chain fatty acids, members of this group of cytosolic proteins were originally identified. The purified recombinant protein showed affinity with fatty acids, in contrast with a mutant which lacks the first 16 N-terminal amino acids. The complete sequence of nucleotides can be described as a primer region beginning by ATG triplet at the height of nucleotides 123-125. The codifying region comprises 399 nucleotides, finishing in position 521. The protein of 133 residues from amino acids has molecular mass 14.847-kDa calculated based on its sequence.

Pérez, J. R. et al, (Perez, J>R., Medina, J. R. R., Blanco, M. A. G. and Hillyer. 1992. "*Fasciola hepatica*: Molecular Cloning, Nucleotide Sequence and Expression of a Gene Encoding a Polypeptide Homologous to a *Schistosoma mansoni* Fatty Acid-Binding Protein". Journal of Experimental Parasitology, Vol. 74: No. 4, pp. 400-407) have proven that a polypeptide that presents cross reactivity with antiserum against immunoprophylactic Fh12 protein, shares significant homology with the *Schistosoma mansoni* 14.8-kDa protein, called Sm14, regarding amino acid sequence (Moser et al, 1991). In addition, it was proved that Fh12 is a potent immunogen and a molecule to be a candidate for immunoprophylaxis of both schistosomiasis and fascioliasis (Hillyer, 1985; Hillyer et al, 1987), as well as an important immunodiagnosis marker in the human fascioliasis (Hillyer et al, 1992). Moreover, the authors were trying to find a recombinant antigen containing Fh15 epitopes and such Fh15 portions could represent the same protein described as being Fh12.

Tendler et al have performed studies of protection against schistosomiasis in mice and rabbits with Sm14 recombinant protein. (1995, 1996). Therefore, the Sm14 protein cDNA was subcloned into pGEMEX-1 vector (Promega). The obtained construction, pGEMEX-Sm14, express Sm14 protein as a fusion with the product from gene 10 of bacteriophage T7 (major T7 capside protein), resulting in a chimeric protein with approximately 45 KDa. After the purification in SDS-PAGE preparatory gels, this fusion protein provided about 50% of protection against *S. mansoni cercaria* infection in experimentation animals, similar to the protection level reached by Saline Extract (SE) from these worms, used as positive control. On the other hand such recombinant protein provided 100% of protection against infection by *Fasciola hepatica* metacercaria (Tendler et al, 1995, 1996), showing that the Sm14 protein can be used as an anthelminthic vaccine. In addition, it is important to mention the U.S. Pat. No. 5,730,984, of the applicant's ownership.

However, during the storage of the Sm14 recombinant protein, the formation of a hardly-controlled precipitate was observed. Moreover, the obtaining of Sm14 recombinant proteins, according to the state-of-the-art, e.g. in pGEMEX, presents disadvantages because it is time-consuming and has low yield for large-scale production.

Thus, there is still a need of obtaining an antigenic material that can be obtained with high yield, in pilot scale, in compliance with GMP guidelines, preserving stability characteristics.

SUMMARY OF THE INVENTION

One objective of the present invention is to obtain an antigenic helminth-derived material, which it is feasible to be generated in recombinant form and used for producing a protein, in pilot scale, in GMP conditions.

Still another objective is related to a more stable mutant forms of the Sm14 protein.

Still another objective of the present invention is the Sm14 molecule defined as a protecting antigen against infections by helminths.

Still another objective of the invention is a vaccine against *Fasciola hepatica* infections in bovine, caprine, and ovine cattle.

It is also objective of the present invention a vaccine against infections by *Schistosoma mansoni* and all other *Schistosoma* species, which are responsible for infections and diseases in humans and animals.

A further object of the present invention is the diagnosis reagent for schistosomiasis and fascioliasis.

BRIEF DESCRIPTION OF THE DRAWINGS

FIG. 2B shows a comparison of the resulting fusions in the plasmids of pRSETA-Sm14, pET3-His-Sm14 and pRSETA-6×His-Sm14 expression.

DETAILED DESCRIPTION OF PREFERRED EMBODIMENTS

The objectives of the present invention are reached by obtaining an antigenic material that provides a protecting immunity against helminth infections of mammal hosts.

In accordance with an aspect of the present invention, mutant forms of the Sm14 recombinant protein were constructed, presenting greater thermal stability and greater stability against chemical denaturant agents, allowing their production in large-scale, where such mutant proteins preserve functional and antigenic properties of the rSm14 protein. It should be emphasized that the rSm14 refers to any recombinant form of the Sm14 molecule, being in form of fusion with other protein or peptide.

According to the present invention, the antigen is selected among several mutant forms from the *Schistosoma mansoni* protein, Sm14, which is capable to stimulate, in mammal hosts, the protecting immunity against helminthological infections, particularly by *Schistosoma mansoni* and *Fasciola hepatica*.

The Sm14 protein has a molecular weight of 14.8 kDa and presents a significant degree of identity with proteins belonging to the family of lipid binding proteins and is characterized by the amino acid sequence below (SEQ ID NO: 1):

```
Met Ser Ser Phe Leu Gly Lys Tpr Lys Leu Ser Glu Ser His Asn Phe Asp Ala
1               5               10                  15

Val Met Ser Lys Leu Gly Val Ser Tpr Ala Thr Arg Gln Ile Gly Asn Thr Val
    20              25                  30                  35

Thr Pro Thr Val Thr Phe Thr Met Asp Gly Asp Lys Met Thr Met Leu Thr Glu
            40                  45                  50

Ser Thr Phe Lys Asn Leu Ser Cys Thr Phe Lys Phe Gly Glu Glu Phe Asp Glu
55                  60                  65                  70

Lys Thr Ser Asp Gly Arg Asn Val Lys Ser Val Val Glu Lys Asn Ser Glu Ser
        75                  80                  85                  90

Lys Leu thr Gln Thr Gln Val Asp Pro Lys Asn Thr Thr Val Ile Val Arg Glu
            95                  100                 105

Val Asp Gly Asp Thr Met Lys Thr Thr Val Thr Val Gly Asp Val Thr Ala Ile
    110             115                 120                 125

Arg Asn Tyr Lys Arg Leu Ser
            130
```

The three-dimensional structure of the Sm14 protein was predicted using molecular modeling from computerized homology, which allowed to identify the potential protecting epitopes and made possible to use the rSm14 of the present invention as a vaccination antigen (Tendler et al, 1996).

Figure 1:
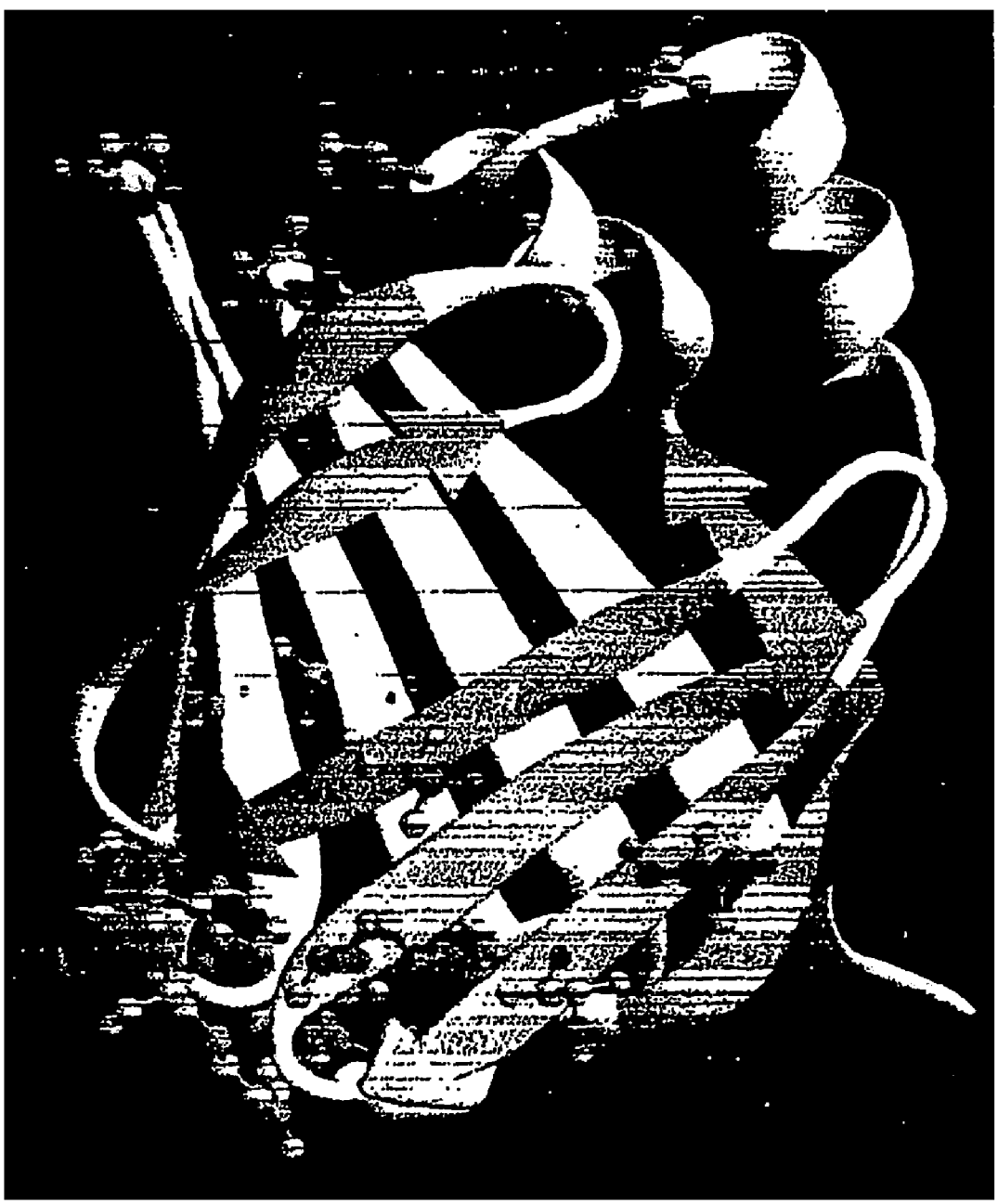
FIG. 1 shows the three-dimensional structure of molecular model for the Sm14 protein.

Molecular models constructed both for Sm14 and Fh15 (the last one being a Sm14-homologous molecule originating from *Fasciola hepatica*, with which shares 44% of sequential identity) show that both molecules adopt three-dimensional configurations that are similar to molecules of other members of lipid-bound protein family ("Fatty Acid Binding Proteins"—FABP). The Sm14 molecular model is composed of 10 antiparallel β-ribbons forming a "barrel-like" structure type (or β-clam) with short connections between ribbons that, generally forming β-loops, as showed in FIG. 1.

The models also allowed previsions on (1) the importance of certain residues provide properties of cross immunogenicity against *S. mansoni* and *F. hepatica*, (as described in the patent application U.S. Ser. No. 10/113,946 and in the U.S. Pat. No. 5,730,984), (2) the residues involved in the interaction with fatty acids and (3) residues that are important for the structural stability and covalent aggregation. The residues involved in the formation of discontinuous epitopes, which are responsible for cross-reaction, are expected as being located mainly in molecule's C-terminal region (approximately starting from the residue 85).

Recombinant mutant proteins of the present invention can be obtained from vectors that allow the expression of Sm14-codifying genes, properly modified, but maintaining the molecule's antigenic characteristic (discontinuous and accessible epitopes located mainly in the Sm14 C-terminal portion).

It will be demonstrated here, the capacity of the Sm14 protein's recombinant mutant forms provide high protection against infections by *Fasciola hepatica* and *Schistosoma mansoni*, as well as all the remaining species of *Schistosoma* and *Echinococcus* and potentially other helminths supposedly pathogenic in relation to humans and animals.

A vaccinal antigen should be a homogeneous parasite-preserved component presenting no great differences in its structure and primary amino acids sequence, so that the immune response against this antigen (and the organism presenting it) be also the most homogeneous and effective in the vaccinated mammal. Therefore, a survey on the gene polymorphism corresponding to any potential vaccinal antigen is a relevant factor to its development. The sequencing performed in original clones (pGEMEX-Sm14) has verified a discrepancy regarding the sequence described by Moser et al. (1991), concerning the amino acid present in the position 20. It was verified that this sequence discrepancy was caused by the existing mutation of the Sm14 protein genomic sequence, due to the natural Sm14 molecule polymorphism.

The analyses of sequences showed two main isoforms for the Sm14 protein: Sm14-M20, whose sequence is identical to the Sm14 protein previously reported to Puerto Rican strain of *S. mansoni* (Moser et al, 1991) and Sm14-T20, where the Met20 codon (ATG) was changed for Thr codon (ACG) (M20T polymorphism).

Obtaining the Sm14-A20 Mutant Form

In order to have control in the experiments of comparison of the structure and function of the Sm14-M20 and Sm14-T20 isoforms, the site-directed mutagenesis of the ACG codon of the T20 in the pRSETA-6×His-Sm14 vector was performed for GCG of the alanine amino acid. Thus, the Sm14-A20 protein was obtained, similar to mutants used in the works of Richieri et al. (1997, 1998) for A-FABP and I-FABP proteins (Fatty Acid Binding Proteins of the adipocyte and intestine, respectively).

Figure 4:
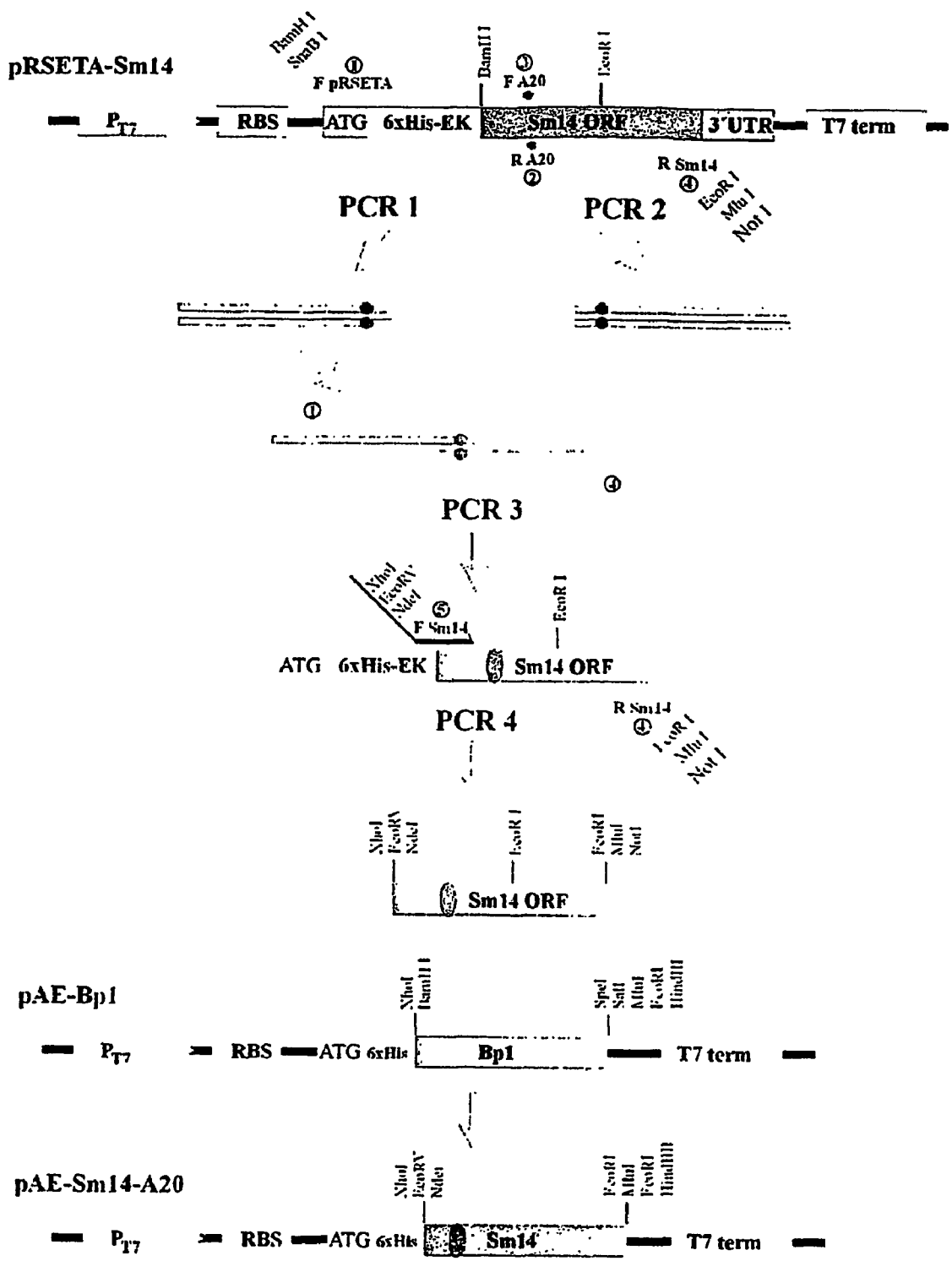
FIG. 4 shows the mutagenesis strategy for obtaining the Sm14-A20 protein.
Figure 5:
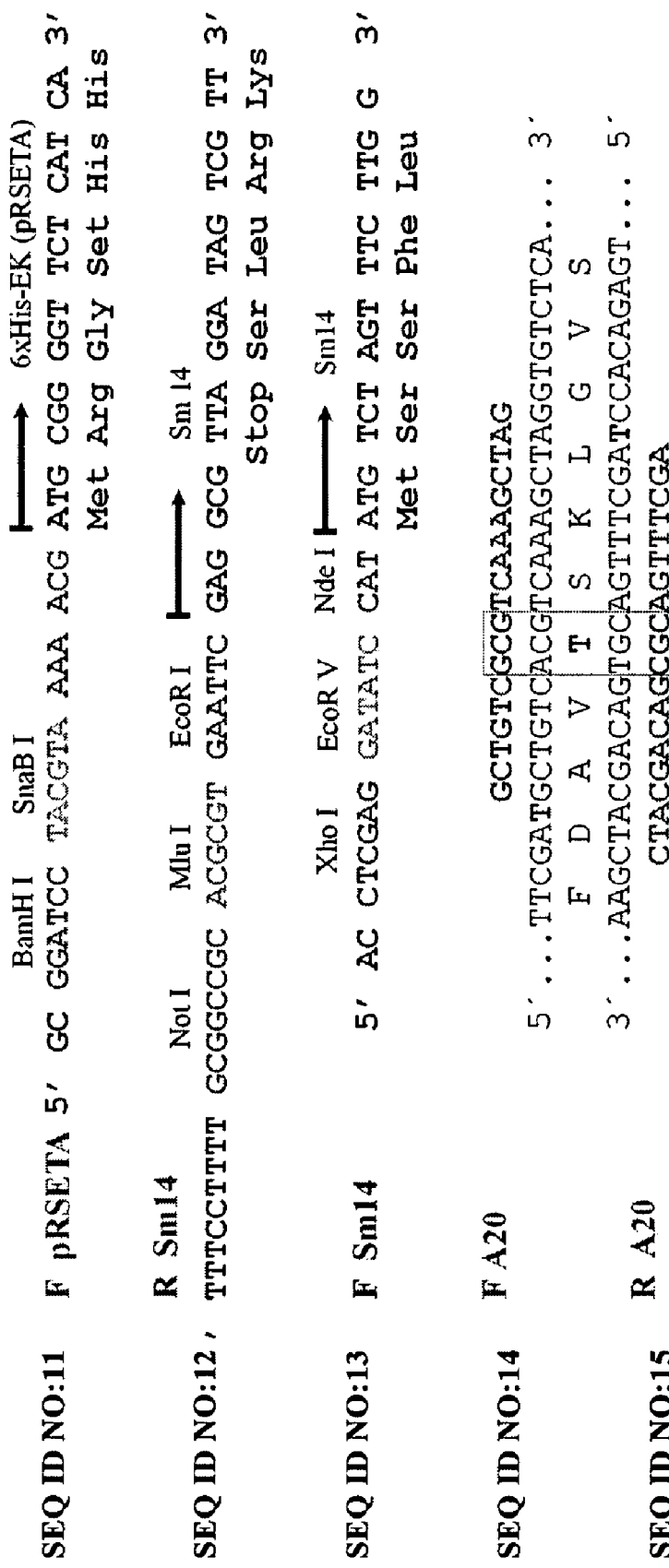
FIG. 5 shows the "primers" used in the process for obtaining the Sm14-A20 mutant form.
Figure 6:
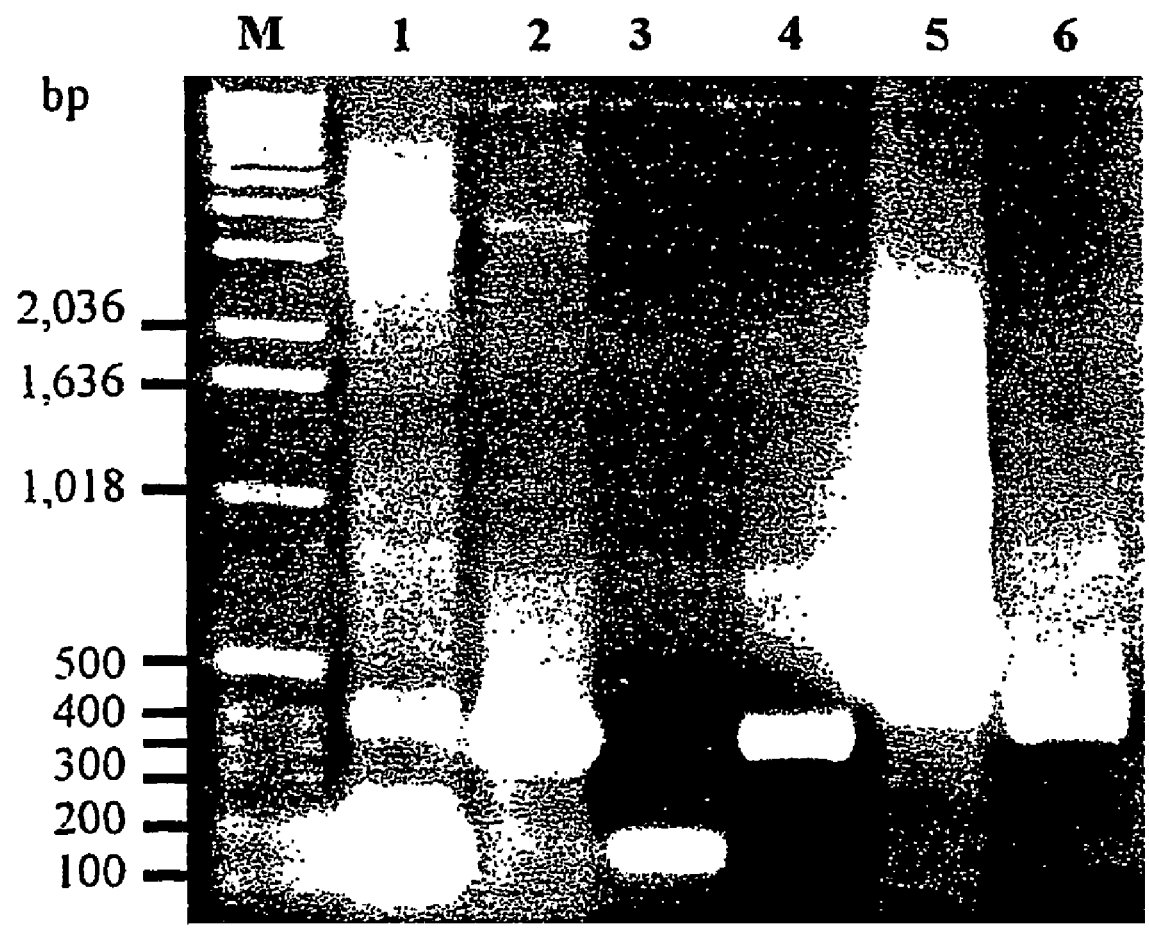
FIG. 6 shows the electrophoretic analysis of products of amplification of the mutagenesis process, where M.—1 Kbp DNA ladder; 1.—product of PCR 1; 2.—product of PCR 2; 3.—amplified of PCR 1 purified; 4.—amplified of PCR 2 purified; 5.—product of PCR 3; 6.—product of PCR 4.
Figure 7:
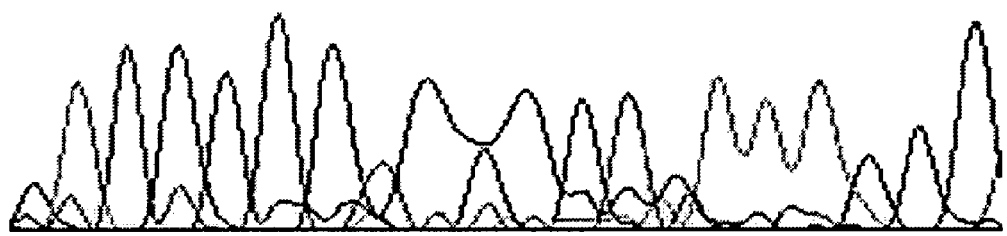
FIG. 7 presents partial sequence of the pAE-Sm14-A20 plasmid, showing the presence of alanine at position 20 of the Sm14 protein.

The strategy of the mutagenesis by PCR for obtaining the Sm14-A20 protein is detailed in FIG. 4. For the choice of F-A20 and R-A20 mutagenic primer sequences showed in FIG. 5 together with the partial sequence of the cDNA of the Sm14 protein, we were careful in order for neighboring nucleotide at extremity 5', were a thymine (showed in bold), once there is a tendency for the Taq DNA polymerase of adding adenine to the extremities 3' of the amplifications. Thus, the adenine added by Taq DNA polymerase in the amplification is supplemented with thymine at the moment of mixing the amplification of the PCR 1 and 2 products. The use of pRSETA-Sm14 as a template and F pRSETA primer facilitate the mutagenesis through the size of the PCR 1 amplification (see FIG. 6). If the pRSETA-6×His-Sm14 is used as a template, the PCR1 would be very small and would not facilitate its purification process. In a last step (PCR 4) we used the F Sm14 and R Sm14 primers. Thus, all proteins, which will be comparatively analyzed will have exactly the same N-terminal fusion, so that comparisons will only depend on the amino acids related to the Sm14 protein. The success of the mutagenesis was confirmed by a restriction analysis and by sequencing, as showed in FIG. 7.

Structure and Stability Analysis of the Sm14 Protein Mutants

Figure 8:
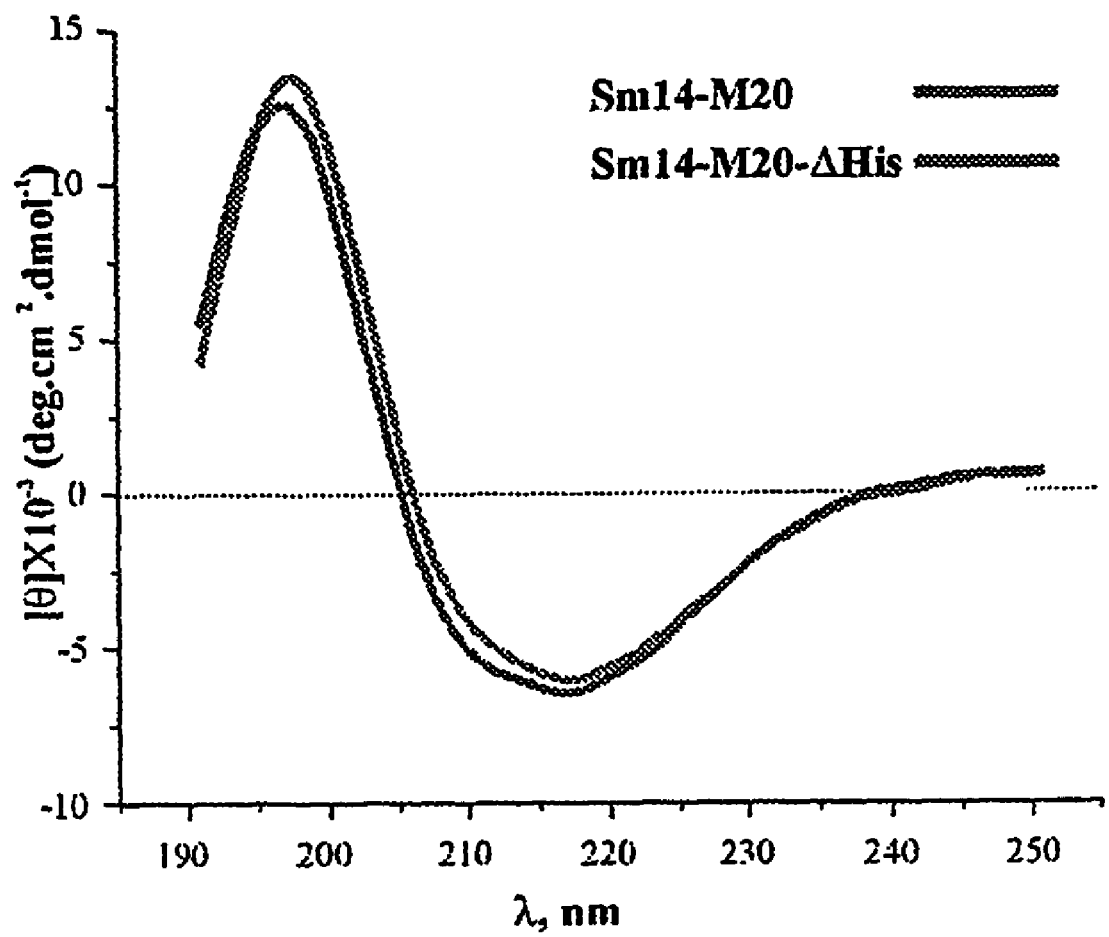
FIG. 8 shows the Circular Dichroism spectrum of Sm14-M20 proteins, where Sm14-M20:—Sm14-M20 protein with the 6×His and Sm14-M20-ΔHis tag.—Sm14-M20 protein without the 6×His tag.

For the study of the structure and stability of the recombinant proteins, CD (Circular Dichroism) spectra at 20° C. were obtained, using 10 μM protein in 10 mM Na-phosphate, pH 7.4 buffer. Initially we compared the Spectra of the Sm14-M20 protein with and without 6×His tag in phosphate buffer (FIG. 8). This analysis has shown that there are no substantial differences in the spectra of both forms, which generate typical spectra of proteins with β-structure conformity, characteristic of the FABPs. Such results are consistent with the modeling of the structure of the Sm14 Protein. As the 6×His tag does not significantly interfere with the structure of the Sm14 protein, the following experiments were performed with the 6×His tag proteins, which are obtained in a larger amount and in a higher degree of purity than the proteins without 6×His tags.

Figure 9:
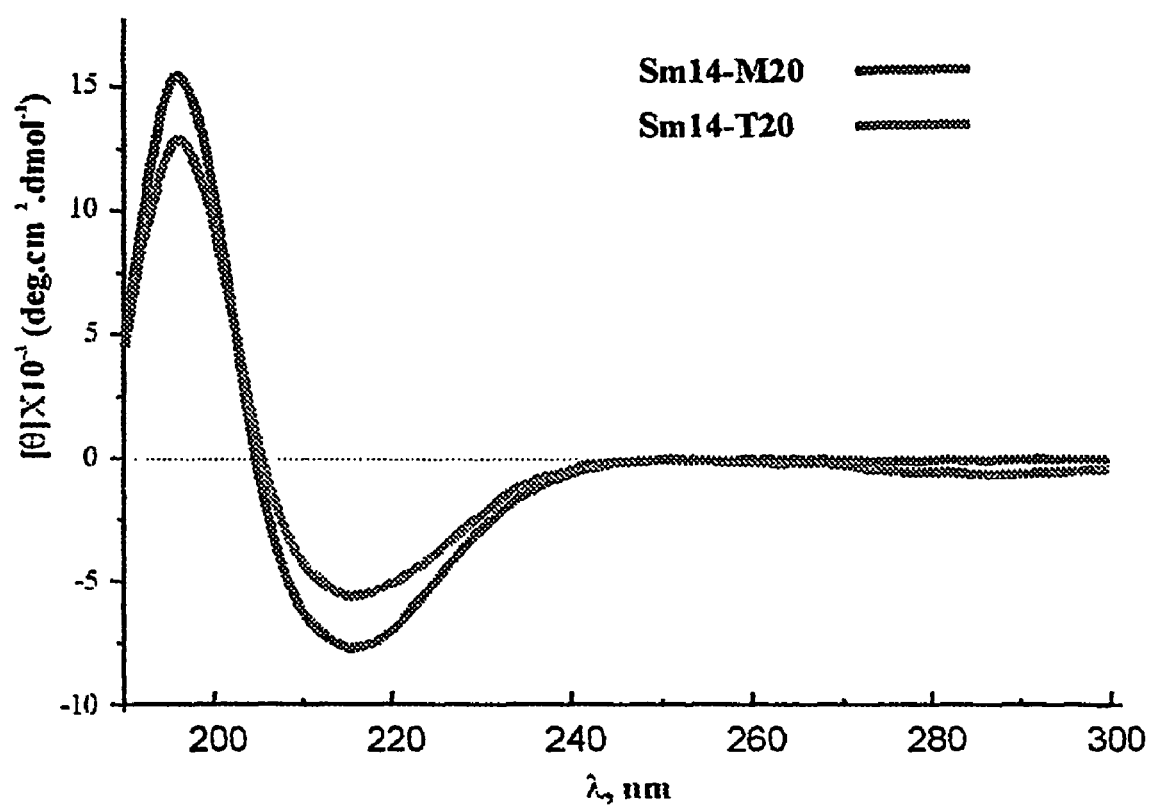
FIG. 9 shows the CD spectrum of Sm14-M20 and Sm14-T20 proteins (with 6×His tag).

In order to study the thermostability of the distinct forms of the Sm14, first CD Spectra of the samples at distinct temperatures were analyzed (data not shown). It was observed that protein gradually loses the β-Structure as the temperature increases until it reaches a spectrum where we observe the loss of the β-structure and an increase of random structure at 80° C. In order to be able to characterize the transition from the native to the denaturant state, we measured the ellipticity (θ) at 216 nm during the change in temperature from 15 to 80° C., as shown in FIG. 9. Such experiments allowed to determine the transition temperature from the native to the denaturant state (melting temperature, Tm) of the proteins. Spectra were also performed at the beginning and end of the temperature changes and a spectrum was also generated after cooling the sample at 15° C. after heating it at 80° C., so as to observe the reversibility of the denaturation of the proteins (FIG. 9 and Table I).

TABLE I

Comparing thermostability Values of Sm14-M20, Sm14-T20, and Sm14-A20 Proteins.

| Protein | [θ] zero, nm (*) | | Δ [θ] zero, nm | % of Renaturation () | Tm in ° C. (*) |
|---|---|---|---|---|---|
| | 15° C. | 15° C. R | | | |
| M20C62 | 204.7 | 202.4 | 2.3 | 82.5 | 55.2 |
| T20C62 | 204.1 | 199.0 | 4.2 | 59.5 | 44.6 |
| A20C62 | 204.6 | 199.0 | 5.6 | 57.2 | 45.8 |

The change in temperature was performed at 1° C. per minute both for the sample heating and for the sample cooling.
(*) The displacement of the spectrum step by [θ] Zero for shorter wavelengths is a sign of loss of β-Structure and appearance of a random structure, 15° C., initial spectrum and 15° C. R spectrum collected after the return of the samples at 15° C.;
(**) The renaturation percentage was arbitrarily determined, by comparing the wavelength of the step by [θ] Zero of the CD Spectra with the value of 191.5 nm (step by [θ] Zero of the spectrum at 80° C., random structure) of the spectra at 15° C. before (100%) and after heating at 80° C. (FIG. 9).
(***) Tm was determined in experiments as the inflection point in the denaturation curve, using the Boltzman Equation of the Microcal Origin ™ program.

The results obtained in the study of the stability of proteins are summarized in Table I. From the comparison of Tm we can conclude that Sm14-T20 and Sm14-A20 proteins are less thermostable (Tm 44.6 and 45.8° C., respectively) than the Sm14-M20 protein (Tm 55.2° C.). Therefore, it is important to notice that a single change of amino acid (M20T) results in a Tm difference of about 10° C. in the Sm14 Protein with a 6×His tag, representing an important gain in thermostability in the case of Sm14-M20. On the other hand, all these proteins cannot renature at the value of 100% after heating at 80° C. and the most affected proteins by heating being the Sm14-A20 and Sm14-T20 forms (57.2 and 59.5% renaturation, respectively), followed by the Sm14-M20 protein (82.5% renaturation).

Such a stability difference was confirmed by using urea as a denaturant agent and by measuring the red shift of the fluorescence of the Tryptophan to characterize the denaturation. For such the samples were diluted in different urea concentrations (0-7M) for a final concentration of 2 μM, excited at 285 nm, and the spectra record ranged from 300 to 400 nm.

Figure 10:
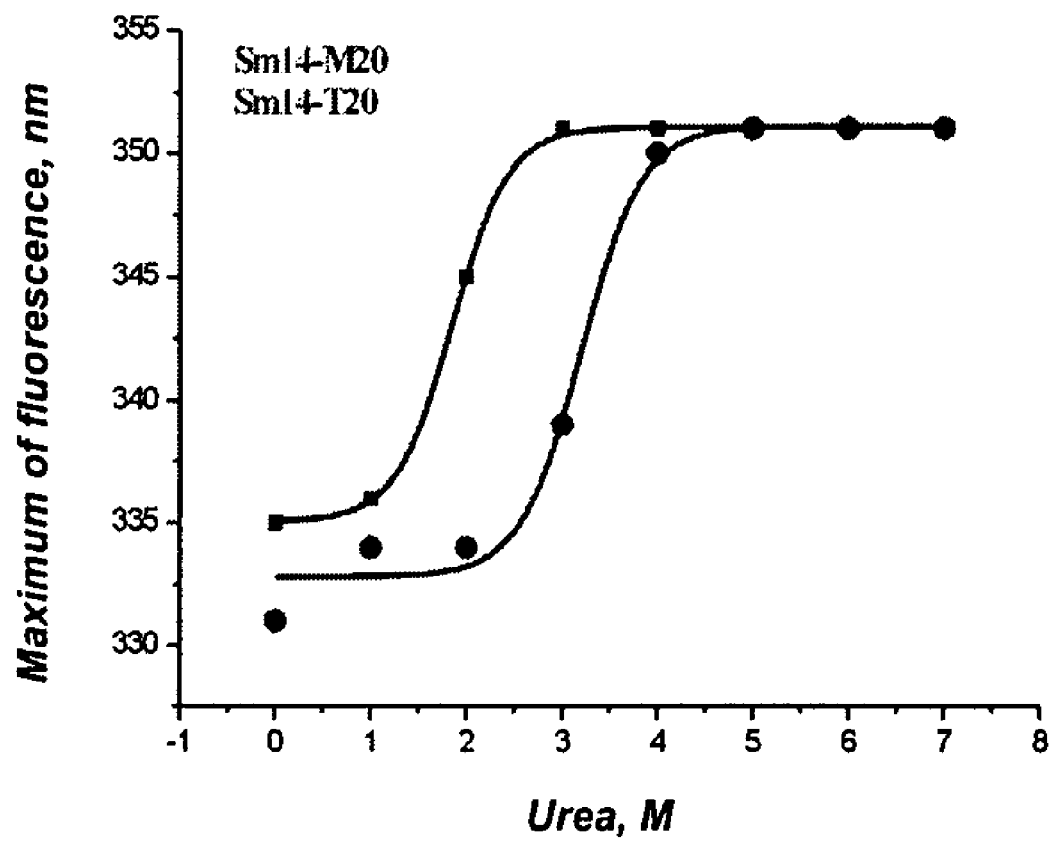
FIG. 10 shows the denaturation of Sm14-M20 and Sm14-T20 proteins by urea.

The data obtained were subjected to a non-linear regression, according to the Boltzman Model of the Microcal Origin™ program. FIG. 10 shows the curves obtained from this analysis. The inflection points on the curves occur in the 1.85 and 3.2M urea concentrations for the Sm14-T20 and Sm14-M20 proteins, respectively, confirming the greater stability of the Sm14-M20 form. With such data we may conclude that the M20T change considerably destabilizes the Sm14 protein before the chemical denaturation with urea.

The data set presented above shows a greater structural stability of the Sm14-M20 isoform compared with the Sm14-T20 or the Sm14-A20 mutant.

Methionine is more hydrophobic and its side chain is longer than threonine and alanine, which may favor the thermodynamic stability of the protein both by entropy (the hydrophobic effect) and by enthalpy (interactions with other residues of the protein through strengths of Van der Waals, etc.), when compared with threonine or alanine in such a position. The Sm14 three-dimensional structure model suggests a less efficient package for alanine or threonine. The last one could lead to a polar group (the hydroxyl of the lateral chain) unsatisfied for hydrogen connections.

Increase of Sm14 Protein's Stability

The vaccinal preparations should be stable to the storage for a time sufficiently extended in order to achieve their destinies with protecting activity. Specifically, the Sm14 protein stability was indeed one of the aspects approached in the present invention.

Observations made over more than 3 months in the stored batches at 4° C. have detected the formation of protein precipitates. Likewise, the level of protection against schistosomiasis decreases with the protein storage time and the sera of animals immunized with the protein recently prepared do not recognize the stored protein (data not showed).

With the purpose of increasing the Sm14 protein stability, we have decided to assess the precipitation causes in some protein preparations.

Figure 11:
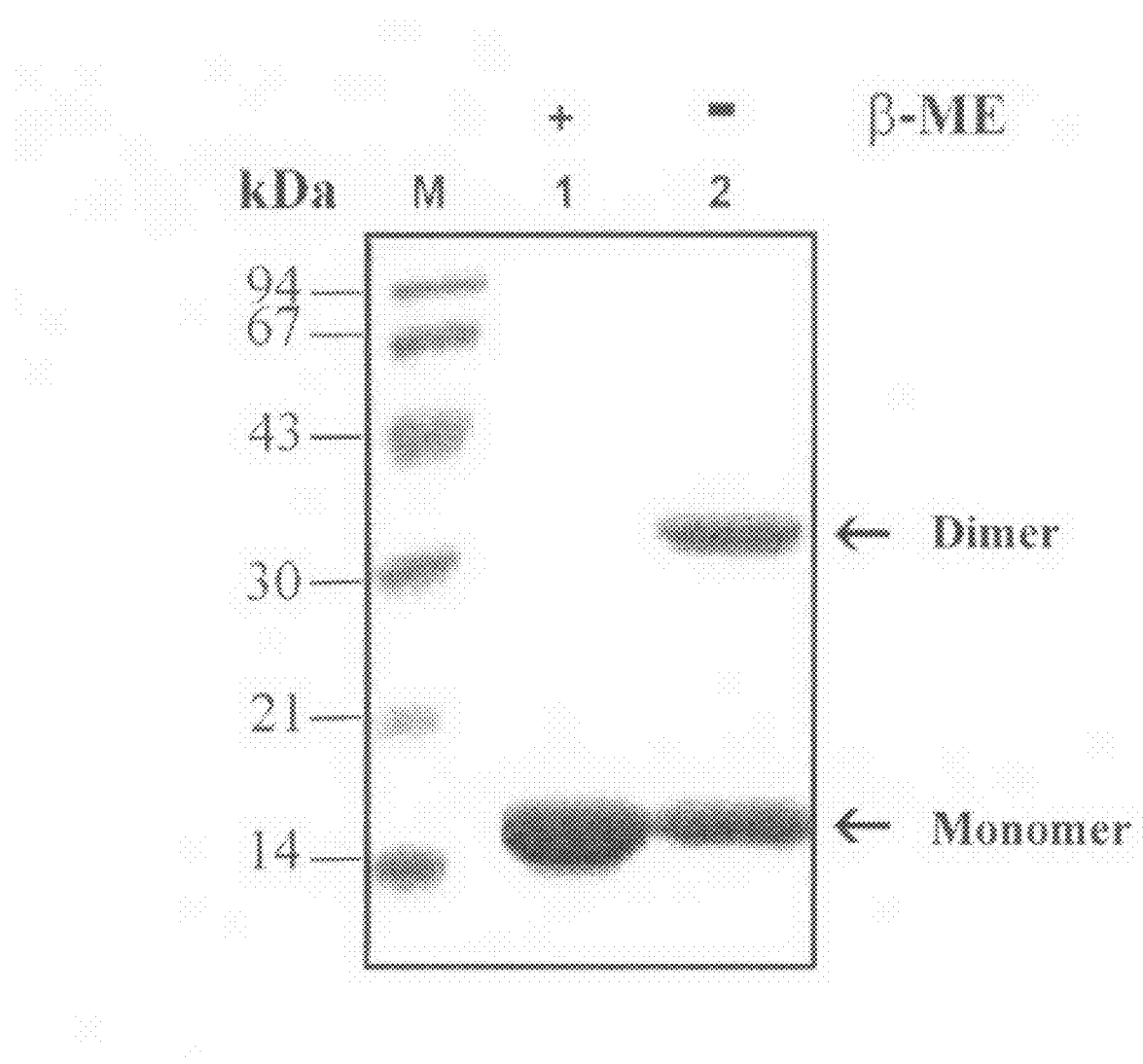
FIG. 11 shows the electrophoretic analysis of the Sm14-T20 protein stored for 3 months at 4° C.

Sm14 preparations that showed precipitation were subjected to electrophoretic analysis. This analysis showed the Sm14-dimer presence originated by the formation of intermolecular disulfide bridges, as showed in FIG. 11. This statement is based on the observation of a single band in the gel (corresponding to Sm14 monomers, Mr ~14.9 kDa) in presence of the lowering agent β-mercaptoethanol and two bands in its absence. In this last case, the second band corresponds to a protein that has molecular mass 2-fold above the Sm14, consistent with the dimer formation through a disulfide bridge. FIG. 11 shows that almost half of the protein is in dimer form.

The Sm14 protein sequence only presents a cysteine residue in position 62, forming the βD-ribbon. In the Sm14 structure, the βD-ribbon does not form hydrogen bridges with the adjacent βE-ribbon. The space between these β-ribbons is filled out by lateral amino acids chains, with the Cys62 participation. The group —SH of the cysteine 62 is not accessible to the solvent. Consequently, the intermolecular dimer formation should occur by loss of the protein β-structure (total or partial denaturation), state that can be stabilized by the formation of the disulfide bridge among proteins at least partially unreeled. The establishment of this bridge possibly determines the irreversibility of the protein denaturation. It was observed that the process of precipitation of Sm14 forms seems to depend on the time and storage temperature, as well as on the concentration of protein preparations. In the Sm14-T20 form, this phenomenon is greater.

In general, one of the problems that affect the stability of recombinant proteins expressed in E. coli is the formation of intermolecular disulfide bridges. For instance, the interferon of human fibroblast is purified in a large amount of E. coli; however, it has little activity and stability compared with the wild type protein. Mark et al. (1984) exchanged a Cys by site-specific mutagenesis, not involved in the formation of intramolecular disulfide bridges, for serine, resulting in a protein with a greater activity and high stability in the course of time. A similar phenomenon was observed with FGF-1 (fibroblast growth factor 1), where the replacement of the three cysteines that are present in the sequence of this protein (140 amino acids) per serine, resulted in an increase of its mean physiological life. Thermodynamic studies revealed no greater thermostability of the mutant proteins; therefore, the longest average lifetime of such proteins was related to the elimination of the reactive sulphydryl group (formation of dimers, oxydation for S-sulphonate).

The presence of the cysteine amino acid is not very common in the FABP family. Thus, the structure of some FABPs is stabilized by intramolecular disulfide bridges, as is the case of the L-FABP of fishes such as *Lepidosiren paradoxa, Lateolabrax japonicum*. The rat L-FABP has a cysteine at position 69 whose side chain is directed towards the inside of the molecule as its low reactivity with DTNB [5.5'acid-ditiobis-(2-nitrobenzoic)] indicates. The rat I-FABP, one of the most studied proteins of the family, does not contain cysteine residues. In a study, changes of amino acids of the polypeptide chain of I-FABP for cysteine were introduced with the intention of using their reactivity with reagents such as DTNB to study the conformational and functional exchanges of this protein (Jiang and Frieden, 1993). One of the exchanges studies was V60C (which correspond exactly to position 62 in the Sm14 Protein), which resulted in a less stable protein than the wild type. On the other hand, the low reactivity of such mutant protein with the DNTB reagent reveals that the residue at such position is directed towards the inside of I-FABP protein in reeled state.

Figure 12:
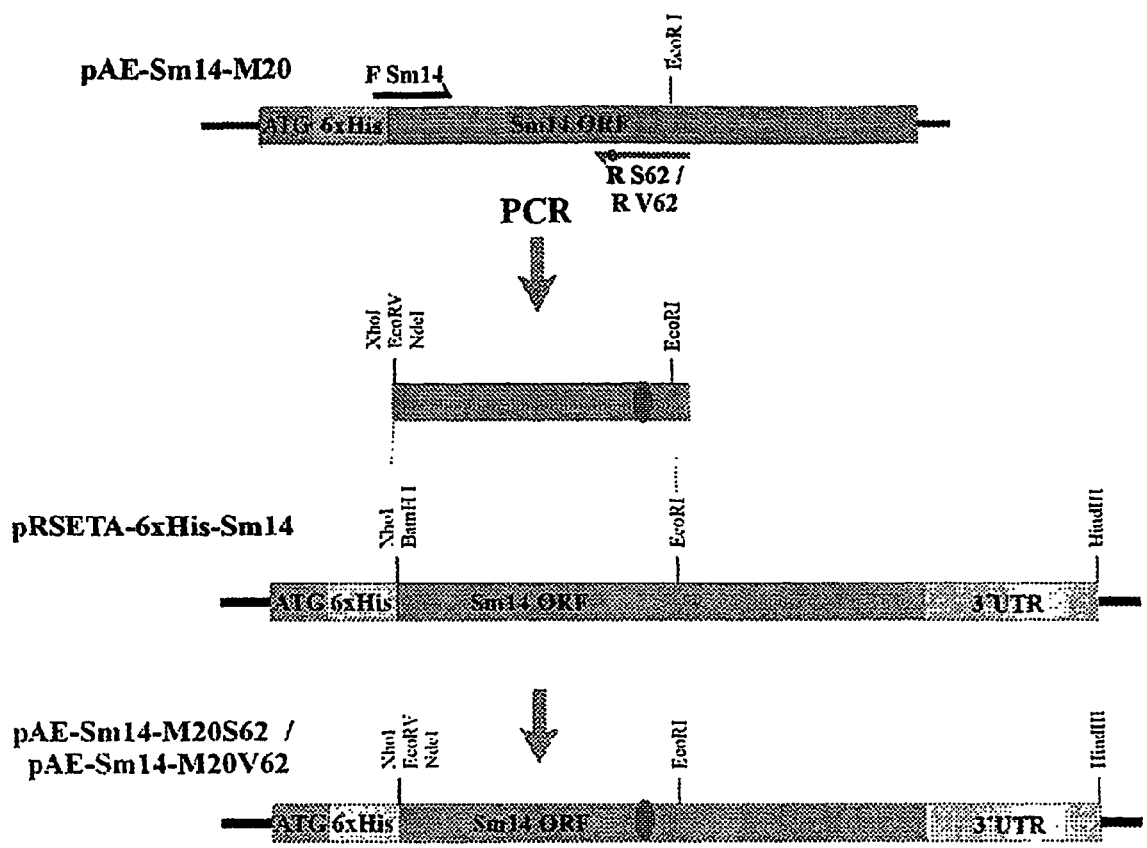
FIG. 12 shows the strategy scheme used for the mutagenesis of the cysteine 62 of the Sm14 protein.

Not being important in the activity of binding the fatty acids and having as an aim abolishing the formation of intermolecular disulfide bridges and other effects of the sulphydryl group, we planned to change cysteine 62 in the Sm14 protein for serine (structural analogue) and for valine (found at such position in *S. japonicum* FABP, which has a high identity with the Sm14 protein and in rat I-FABP). For this purpose we performed a site-directed mutagenesis by PCR, in conformity with the strategy showed in FIG. 12.

The primers used for mutageneses, besides primer FSm14 already described, were:

SEQ ID NO:6 primer R S62: 5' TCGAATTCCTCGCCGAACTTGAACGT AGAAGAAAG 3'.

SEQ ID NO: 7 primer R V62: 5' TCGAATTCCTCGCCGAACTTGAACGT AACAGAAAG 3'.

The EcoRI enzyme recognition site is in bold; the position of the codon of the amino acid at position 62 is underlined. The nucleotides changed for Cys62 (TGT codon) for Ser (TCT) or Val (GTT) mutations are emphasized in bold italics.

Figure 13:
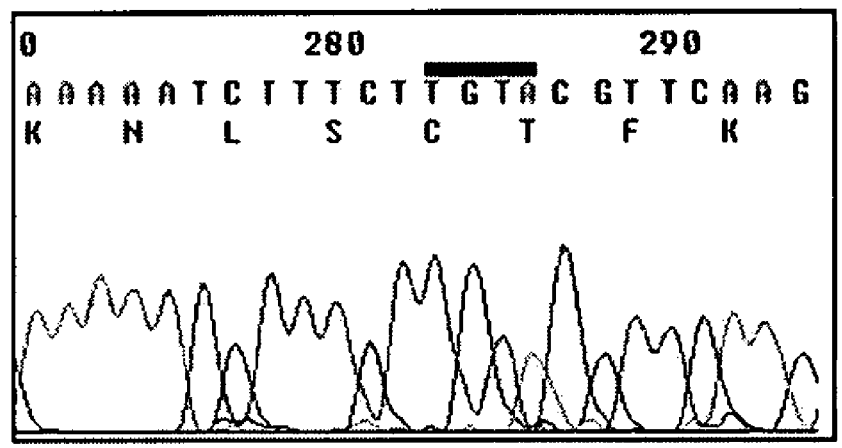
FIG. 13 shows a comparison of partial sequencing of the Sm14 mutant forms, showing the mutagenesis sites (showed by the full bar).
Figure 13:
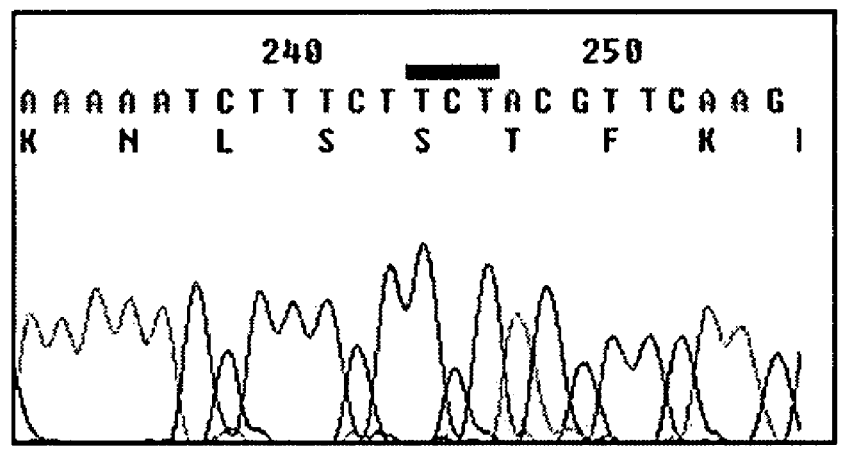
Figure 13:
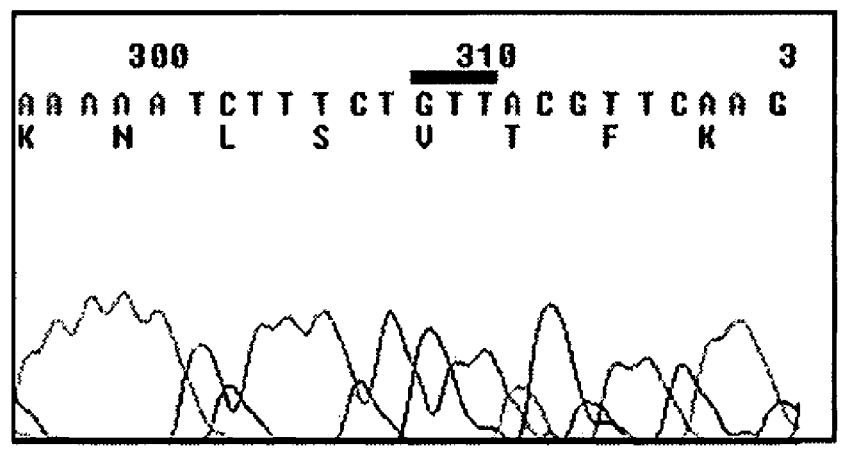

The constructs obtained were analyzed by restriction, performing digestions with the EcoRV endonucleases (resulting from the insert) and HindIII (contained in the Vector). The release of the insert of approximately 600 bp indicated the success of the constructions. The mutageneses were confirmed by sequencing, as showed in FIG. 13. The resulting plasmids were called pAE-Sm14-M20S62 (exchange C62S) and pAE-Sm14-M20V62 (exchange C62V).

Figure 14:
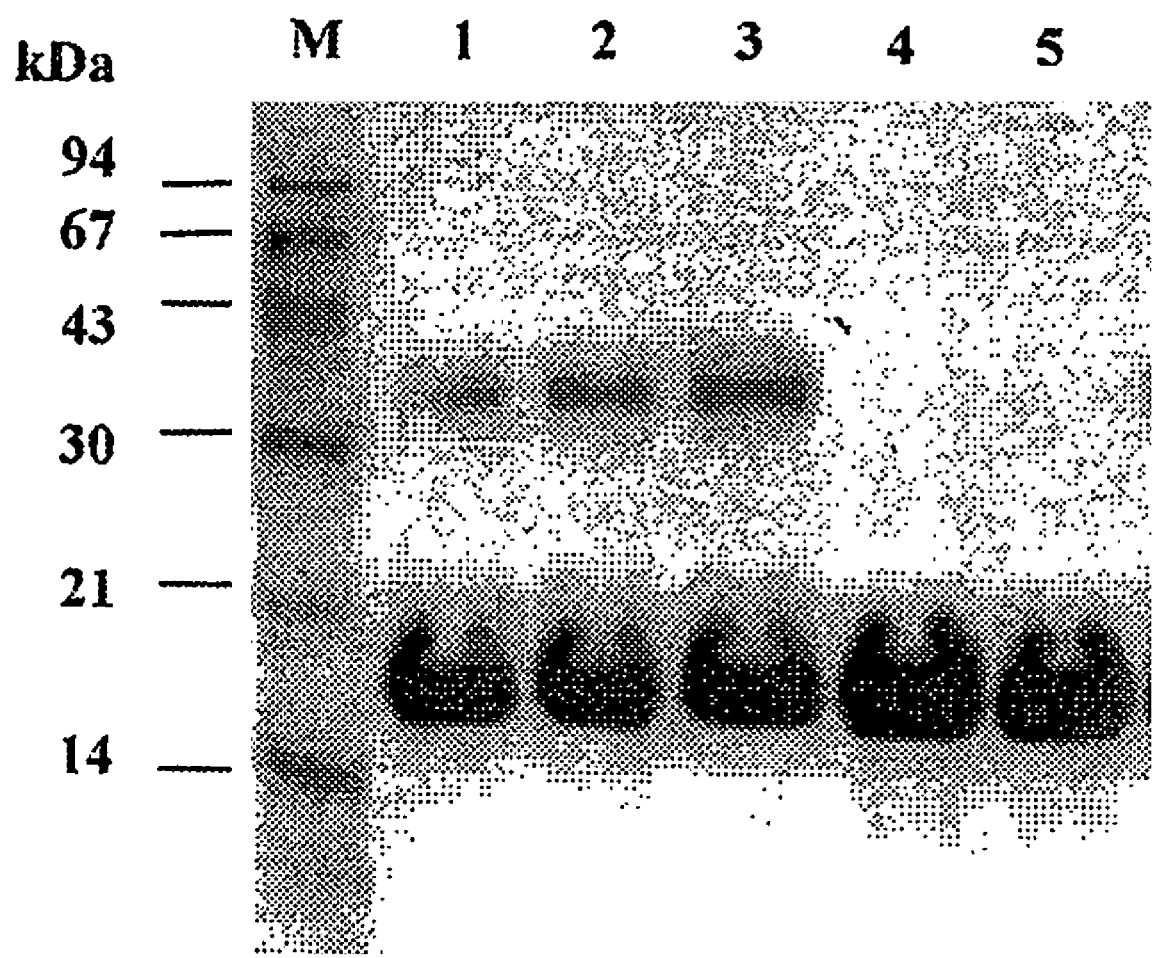
FIG. 14 shows a comparison between the distinct forms of the Sm14 protein, in non-reducing conditions, where M.—Marker of molecular mass; 1.—Sm14-M20; 2.—Sm14-T20; 3.—Sm14-A20; 4.—Sm14-M20S62; 5.—Sm14-M20V62. All the Sm14 proteins have 6×His tag. To induce the dimer formation, the samples were heated at 95° C. for 5 minutes.

The Sm14-M20S62 and Sm14-M20V62 proteins were expressed and purified from E. coli BL21 (DE3) strain cultures, transformed with the pAE-Sm14-M20S62 or pAE-Sm14-M20V62 plasmids, using the same procedures previously described for 6×His Tag proteins. The yields in terms of amount and purity were the same as for all Sm14 forms. FIG. 14 shows the electrophoretic analysis of the proteins in non-reducing conditions.

In such analysis we can observe the absence of dimers in the proteins where cysteine 62 was replaced by serine or valine, indicating the success of the mutagenesis and that aim of eradicating the formation of dimers has been achieved.

Figure 15:
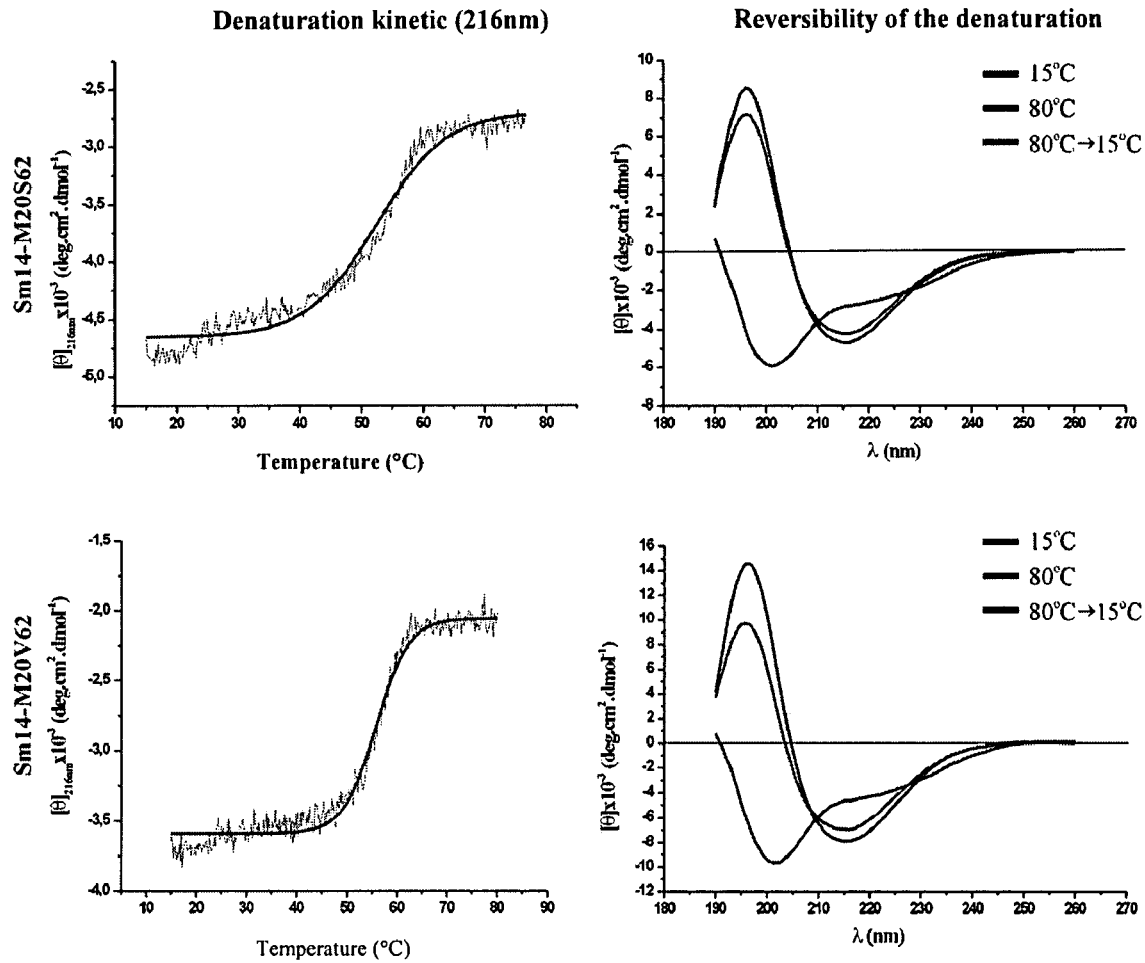
FIG. 15 shows the thermostability of Sm14-M20S62 and Sm14-M20V62 proteins.

Afterwards, we studied the Sm14-M20S62 and Sm14M20V62 thermostability, using the methodology previously described for the Sm14-M20 and Sm14-T20 isoforms through circular dichroism. The CD spectra of the Sm14-M20S62 and Sm14-M20V62 mutants revealed that they maintain the β-Structure similar to the native Sm14 Protein. FIG. 15 shows the denaturation curves through the temperature of the Sm14-M20S62 and Sm14-M20V62 mutant proteins.

With such data we calculated the Tm of the Sm14-M20S62 and Sm14-M20V62 mutants and the percentage of renaturation which are presented in Table II, where the results of thermostability obtained are summarized for all forms of the Sm14 protein discussed in the present invention.

The denaturation was assessed by ellipticity at 216 nm during titration with the temperature. At the beginning (15° C.) and at the end (80° C.) CD spectra were obtained (in blues and red, respectively). One last spectrum was collected after the return of the samples at 15° C. (in green), in order to characterize the capacity of protein renaturation (compare with FIG. 10).

TABLE II

Comparison of thermostability values in distinct forms of the Sm14 protein

| Protein | [θ] zero, nm (*) 15° C. | [θ] zero, nm (*) 15° C. R | Δ [θ] zero, nm | % of renaturation (*) | Tm in °C. (*) |
|---|---|---|---|---|---|
| M20C62 | 204.7 | 202.4 | 2.3 | 82.5 | 55.2 |
| T20C62 | 204.1 | 199.0 | 4.2 | 59.5 | 44.6 |
| A20C62 | 204.6 | 199.0 | 5.6 | 57.2 | 45.8 |
| M20S62 | 204.6 | 204.4 | 0.2 | 98.5 | 52.5 |
| M20V62 | 204.6 | 203.8 | 0.8 | 93.9 | 55.8 |

(*) Data calculated as described in Table I.

From such data we concluded that the exchange of Cysteine 62 in the Sm14-M20 protein for serine (Sm14-M20S62) does not result in a molecule with greater thermostability as can be seen by the slight Tm difference between such forms. In the case of the Sm14 protein, the Sm14-M20S62 mutant form is slightly less thermostable than the wild type protein (Sm14-M20) but the renaturation of such mutant form was greater than in the case of Sm14-M20 as can be observed by comparing the CD spectra before and after heating (FIG. 15, Table II), which can be associated with the elimination of the chemical effects of the sulphydryl group (already mentioned) during the heating of proteins, which would make the denaturation process irreversible, as observed for FGF-1 protein.

The exchange of cysteine 62 for valine (Sm14-M20V62) resulted in a slightly more thermostable protein than Sm14-M20. The results showed here are similar to those obtained in the comparison of the V60C mutant with the I-FABP wild type protein (Jiang and Frienden, 1993), where the insertion of the cysteine group resulted in a less stable protein.

Stability of Sm14 Protein Forms

The aim of this part of the work was to obtain more stable proteins along the time. Therefore, we studied through circular dichroism the stability of the Sm14-M20, Sm14-T20, and Sm14-M20S62 proteins stored at 4° C. for two months. The approximate concentration of proteins was 70 μM. Results of such experiments are summarized in FIG. 16 where we show that the Sm14-M20S62 protein loses the intensity of its spectrum along the time, maintaining, however, the β-Structure, unlike the Sm14-M20 proteins (FIG. 15) and Sm14-T20 (data not showed) which lost β-Structure during storage.

Figure 17:
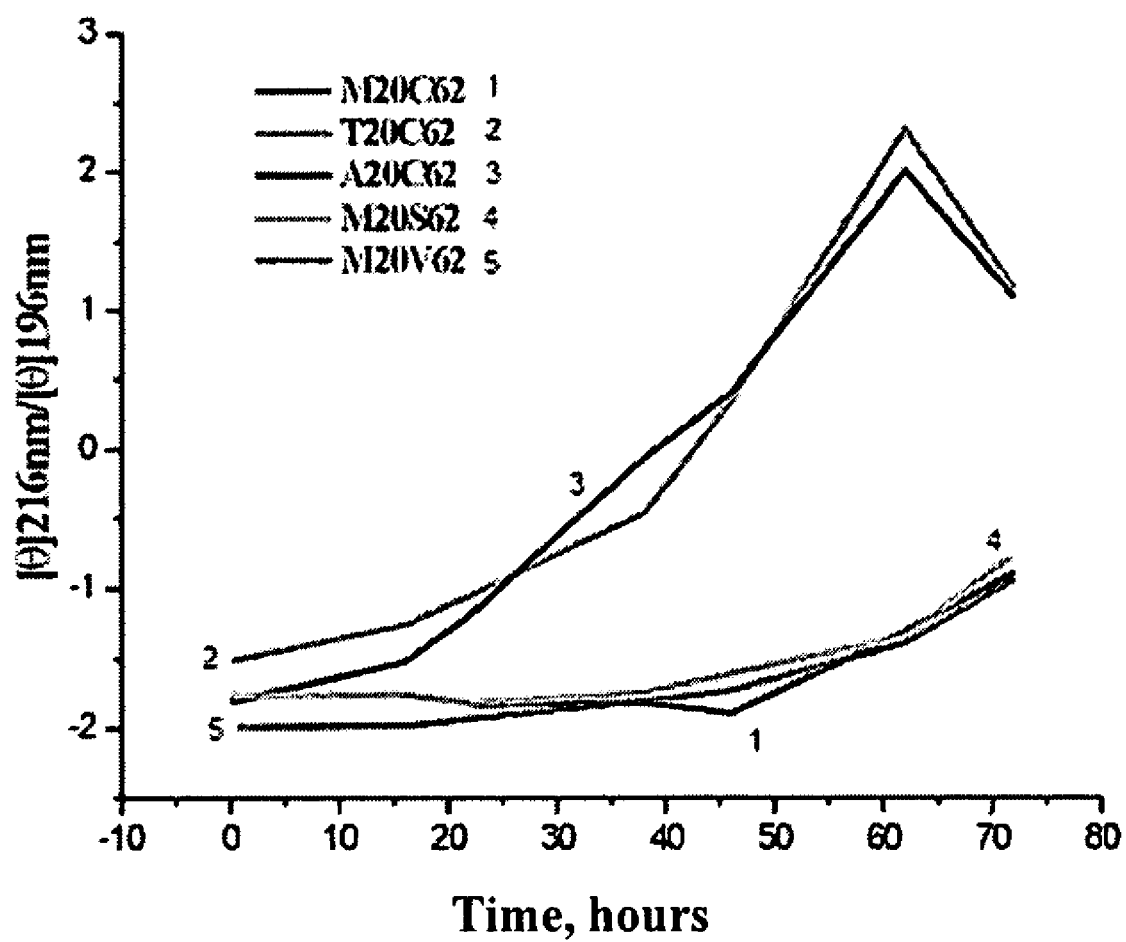
FIG. 17 shows stability of isoforms and mutants of the Sm14 protein at 28° C.

Afterwards, in order to accelerate the β-Structure loss process, the Sm14-M20, Sm14-T20, Sm14-A20, Sm14-M20S62, and Sm14-M20V62 proteins were incubated at 28° C. for 80 hours. The concentration of proteins was 10 μM for the collection of CD spectrum. CD Spectra were collected at time intervals of 8 to 12 hours. It was observed that the β-Structure profile is maintained; however, with less intensity of the bands. Based on these spectra, the β-Structure was characterized, independently of the CD spectrum intensity. The 216 nm/196 nm molar ellipticity relation was used to this end. FIG. 17 shows the analysis of the results of such experiments.

Figure 16:
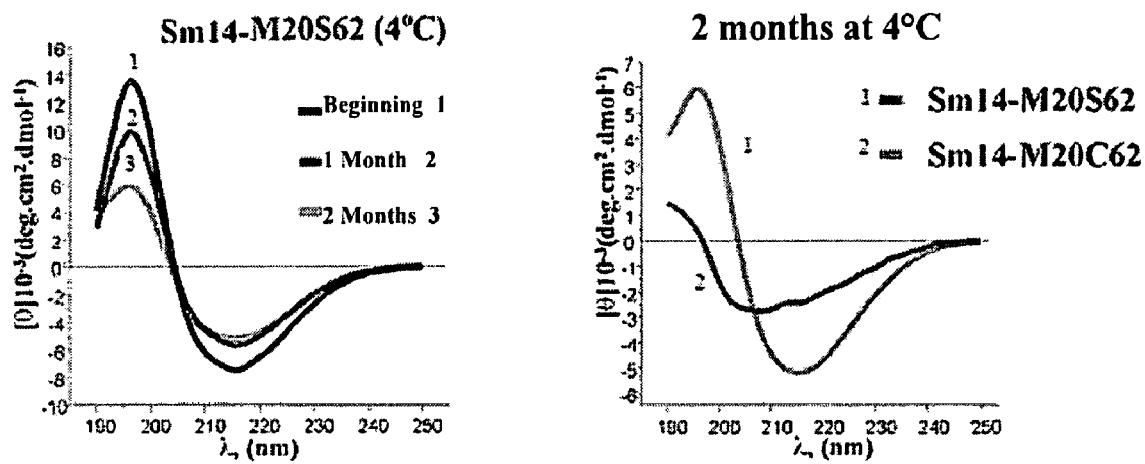
FIG. 16 shows the stability of Sm14-M20C62 and Sm14-M20S62 proteins at 4° C. in the course of time.

The deviation in the 216 nm/196 nm molar ellipticity relation of the −2 value (approximately) indicates loss of β-Structure and its alteration to positive values indicates formation of random structure. The decrease in the intensity of the curves of the Sm14-T20 and Sm14-A20 forms after 60 hours provides evidence of the protein aggregation (FIG. 16). In such conditions, the Sm14-T20 and Sm14-A20 proteins lost β-Structure after 37 hours, whereas the Sm14-M20, Sm14-M20S62, and Sm14-M20V62 maintained β-Structure along the experiment time. Such data agree with the observation of the fact that the Sm14-M20 protein is more stable than the Sm14-T20 protein during storage.

It is worth pointing out that according to the Tm determined for proteins, 28° C. would affect the Sm14-T20 and Sm14-A20 forms more intensely. Thus, in order to differentiate the stability of the Sm14-M20, Sm14-M20S62, and Sm14-M20V62 forms along the time, a higher temperature as well as a higher concentration of proteins were used. Taking into account the storage data at 4° C., we hope that in more restrictive conditions the Sm14-M20 protein will also lose the β-Structure, whereas Sm14-M20S62 and Sm14-M20V62 forms shall be more stable. Thus, observations made during the analysis of the data from nuclear magnetic resonance, with the Sm14M20, M20S62, and M20V62 proteins, expressed and purified with no 6×his Tag, show that the Sm14-M20V62 form kept itself more stable (did not precipitate) at high concentrations (approximately 1 mM) and during one month at 20° C.

The stability along the time has a direct relation with the renaturation capacity of recombinant proteins after heating at 80° C. Thus the elimination of the sulphydryl group of the Sm14 protein also resulted in proteins with a greater stability in the course of time. It is possible that during storage at 4° C. or 28° C., proteins may lose their tertiary conformity and βD- and βE-ribbons be separated, so that the sulphydryl group of cysteine may be oxidized or interacts with similar groups of other proteins in the same state, becoming thus stabilized the loss of β-Structure. On the other hand, the stability of proteins along the time does not depend on the protein thermostability. Such data may be of importance to plan mutants with a longer average lifetime in other proteins.

Thus, the aim of obtaining a more stable variant of Sm14 has been achieved. In this respect, the Sm14-M20V62 protein (the mutant with higher stability) presents itself as a further candidate as a vaccinal model against schistosomiasis and fascioliasis.

Protection experiments using Sm14 mutant proteins of the present invention, against helminth infections, are presented below.

Materials and Methods

Figure 2A:
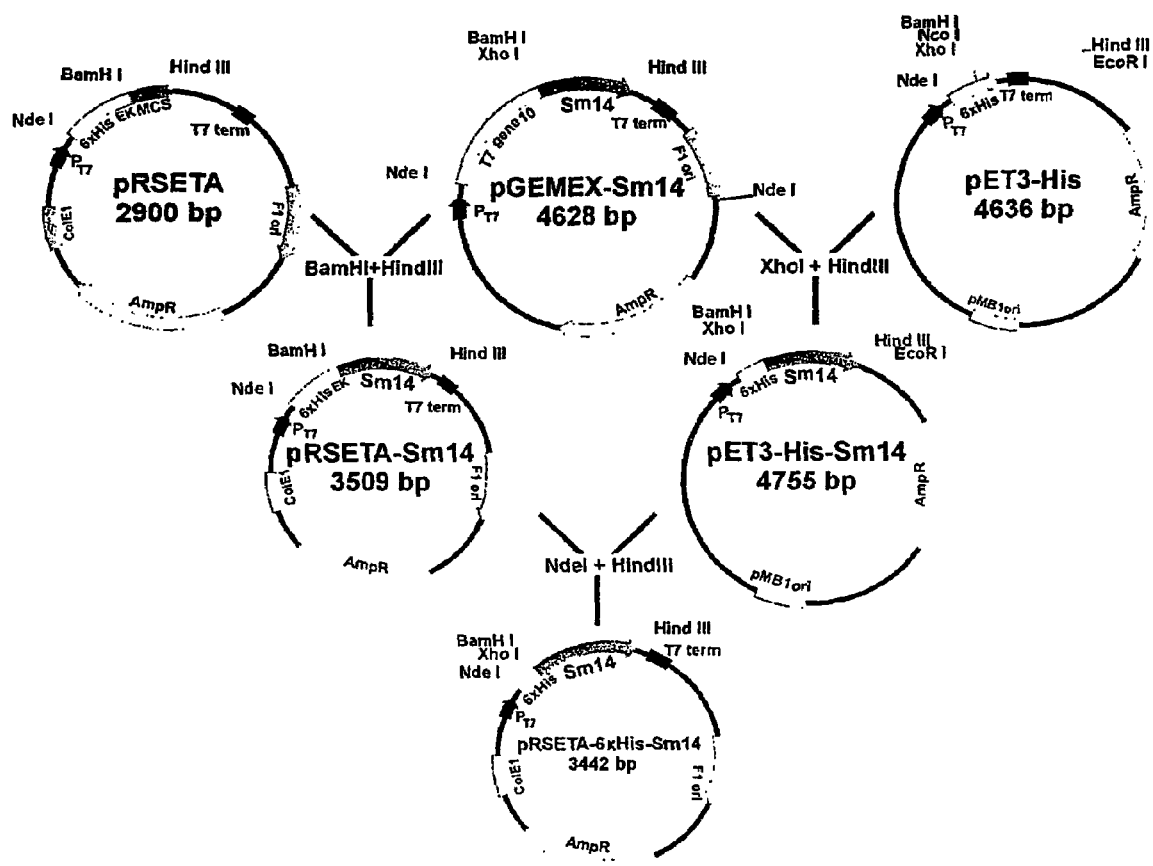
FIG. 2A shows the strategy of subcloning the Sm14-protein cDNA in vectors of pRSETA and pET3-His expression and obtaining the vector of pRSETA-6×His-Sm14 expression.

The process for obtaining, characterizing, and purifying the recombinant Sm14 was described in Mem. Inst. Oswaldo Cruz, Rio de Janeiro, Vol. 96, Suppl.: 131-135, 2001, and it is detailed in FIGS. 2A and 2B.

Figures 3A, 3B:
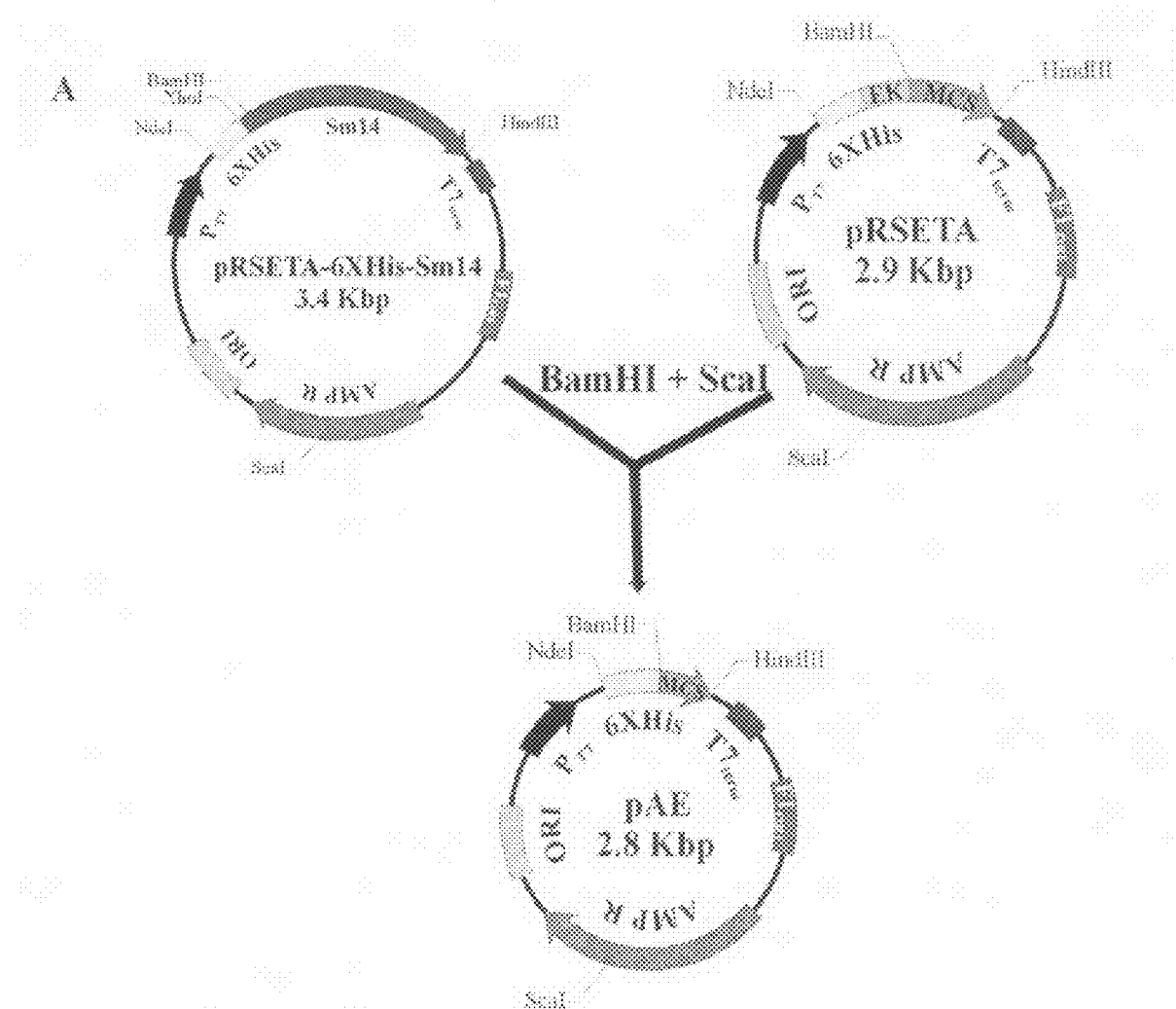
FIGS. 3A and 3B show the obtaining of the vector of pAE expression (FIG. 3A) and its multiple site of cloning (FIG. 3B).

Another process for obtaining the characterization and purification of the Sm14 recombinant protein is detailed in FIGS. 3A and 3B.

The evaluation of the protecting activity of the recombinant proteins was performed according to the Examples below.

According to the present invention, the amount of proteins used in animals to provide protection against helminths may range widely and it is closely related to the weight and species of the receiver animal and to the helminth against which we want to induce protection. Preferentially, the said amount ranges from 1 μg to 1000 μg.

EXAMPLE 1

Example 1 presents a comparative table among protection results obtained in mice, with several mutant forms constructed and obtained from the rSm14.

The vaccination protocol was performed as below.

| Group | 0 day | 7 days | 28 days | 88 days | 133 days |
|---|---|---|---|---|---|
| Vaccinated | V | V | V | C | P |
| Control | | | | C | P |

Where:
V means vaccination;
C means challenge; and
P means perfusion (for recovery adult worms and evaluation of the protection).

Comparative Table

| Experimental Groups | N | Adult Worms Min | Adult Worms Max | X ± SEM | Protection |
|---|---|---|---|---|---|
| Sm14TC + Ribi (1 exp.)* | 12 | 12 | 28 | 18.6 + 0.45 | 24.10% |
| Sm14TC + Alum (4 exp) | 47 | 2 | 26 | 13.8 + 0.14 | 43.70% |
| Sm14TC (3 exp) | 34 | 6 | 36 | 18.3 + 0.19 | 25.30% |
| Sm14AC + Alum (1 exp) | 14 | 6 | 34 | 19.4 + 0.6 | 20.80% |
| Sm14AC (1 exp) | 13 | 10 | 36 | 20.1 + 0.6 | 17.90% |

-continued

| Experimental Groups | N | Adult Worms Min | Max | X ± SEM | Protection |
|---|---|---|---|---|---|
| Sm14MS + Alum (2 exp) | 22 | 2 | 24 | 11.2 + 0.3 | 54.30% |
| Sm14MS (1 exp) | 15 | 0 | 20 | 10.6 + 0.4 | 56.70% |
| Sm14MV + Alum (2 exp) | 28 | 2 | 22 | 11.8 + 0.5 | 51.80% |
| Sm14MV (1 exp) | 12 | 6 | 24 | 15.2 + 0.5 | 38.00% |
| Sm14TI + Alum (2 exp) | 28 | 4 | 24 | 10.6 + 0.2 | 56.70% |
| Sm14TI (1 exp) | 12 | 4 | 22 | 14.0 + 0.4 | 43.00% |
| Sm14MC + Alum (2 exp) | 25 | 0 | 20 | 8.16 + 0.2 | 66.70% |

-continued

| Experimental Groups | N | Adult Worms Min | Max | X ± SEM | Protection |
|---|---|---|---|---|---|
| Sm14MC (1 exp) | 13 | 6 | 20 | 12.9 + 0.3 | 47.40% |
| Adjuvant (9 exp) | 120 | 6 | 44 | 22.5 + 0.06 | 0% |
| PBS (Phosphate Buffered Saline) (9 exp) | 118 | 8 | 46 | 24.5 + 0.06 | |

Where:
N means the number of animals per experimental group and
X ± SEM means the standard mean plus or minus the standard error.
The mean protection for each group of animals (immunized/challenged animals and respective controls) is calculated as follows.
P = (C − V)/C × 100 where C=recovered parasites of the controls; V=recovered parasites of the vaccinated animals and P=protection.

The adjuvants used according to present invention may be selected among Alum, Freund's adjuvant, MPL+TDM (monophosphoryl lipid A+trehalose dicorynomycolate), MPL+TDM+CWS, or Quil A; however, any other similar adjuvants may be employed in the formulation.

The Comparative Table above shows that mutant proteins constructed (Sm14-M20S62 and Sm14-M20V62) present protection levels comparable with the Sm14-M20 original protein (Sm14-M20C62). The advantage of mutants, in their use as a base of a helminth vaccine, does not lay in providing higher protection levels but in maintaining the structural integrity of the vaccine's active ingredient (Sm14) and for more time.

EXAMPLE 2

Example 2 presents the protection results obtained in mice, with the several mutant forms constructed and obtained from the rSm14. The methodology used in Example 2 was identical to Example 1.

A hundred metacercaria/mouse were used in the challenge. The vaccination was performed using three 10-μg doses of the protein, according to the same protocol described in Example 1.

Results

| Sm14TC | Sm14MS | Sm14MV | Sm14TI | Sm14MC | Adjuvant | PBS |
|---|---|---|---|---|---|---|
| 2 | 2 | 4 | 6 | 0 | 10 | 10 |
| 2 | 6 | 4 | 6 | 0 | 12 | 10 |
| 4 | 6 | 6 | 6 | 0 | 12 | 14 |
| 4 | 6 | 6 | 8 | 2 | 12 | 14 |
| 6 | 10 | 6 | 8 | 4 | 16 | 14 |
| 6 | 12 | 8 | 8 | 4 | 16 | 16 |
| 6 | 12 | 8 | 10 | 4 | 16 | 16 |
| 8 | 12 | 8 | 10 | 4 | 16 | 18 |
| 8 | 14 | 12 | 10 | 6 | 18 | 18 |
| 12 | 14 | 14 | 10 | 6 | 20 | 20 |
| 14 | 9.4 | 14 | 12 | 8 | 22 | 22 |
| 14 | 44.70% | 14 | 12 | 8 | 22 | 22 |
| 16 | | 16 | 16 | 10 | 26 | 22 |
| 18 | 18 | | 9.384615 | 10 | 28 | 22 |
| 8.571429 | | 9.857143 | 44.80% | 10 | 17.57143 | 17 |
| 49.60% | | 42.40% | | 5.066667 | 0% | |
| | | | | 70.20% | | |

The whole numbers (0 to 28) represent the number of worms recovered, per mouse and per vaccinated group. The mean result (worms/mouse average) found (i.e., Sm14TC 8.571429) is obtained through the sum of the number of recovered worms divided by 14 (n=14).

EXAMPLE 3

Example 3 shows the data from the experiment of vaccination in mice with mutants of the Sm14 protein against *F. hepatica*. The challenge was performed using 3 metacercaria. The numeric results are presented in the following way:

Number of animal with liver lesion/Number of the living animals at the end of the experiment.

| Exp. | Protein | No. of animal with liver lesion | No. of the living animals at the end |
|---|---|---|---|
| 1 | TI (T20C62) | 2 | 18 |
| 2 | A20C62 | 4 | 18 |
| 3 | T20C62 | 4 | 17 |
| 4 | M20C62 | 5 | 20 |
| 5 | M20S62 | 4 | 15 |
| 6 | M20V62 | 7 | 16 |
| Control | — | 17 | 17 |

No antigens were administered for the control group that only received the infection simultaneously to the vaccinated groups.

From the results above, it is possible to observe that mutant forms of the Experiments 5 and 6, more stable than the wild type form (Cys62), have provided protection for vaccinated animals. It is worth pointing out that although the mutant forms have not reached high rates of protection in its wild type form (Cys62), these new mutant forms can perfectly be obtained in large-scale, since a renaturation of approximately 100% was reached. Moreover, the final result (%) cannot be considered separately and it is also important to observe the vaccination impact in reducing the pathology.

As already mentioned previously, the primary objective of the present invention was the development of new mutant forms of the Sm14 protein, for producing a greater production volume. In this sense, expression and purification systems in *Escherichia coli* were used for the Sm14 protein with a fusion of 12 amino acids in the N-terminal extremity and without fusion. The purity and yield of the Sm14 protein in these systems were higher than the previously obtained with the pGEMEX-Sm14 plasmid, allowing the production of this protein in larger scale.

The recombinant proteins here obtained were capable to provide protection against the infection by *S. mansoni* cercaria.

As for the M20T polymorphism in the physiology of *S. mansoni* worms, a structural and functional association of the Sm14 protein and the protein group comprised by adipocyte FABP, brain, heart, epithelium, and CRBPs was established.

It was found that the single cysteine at the position 62 of the Sm14 protein could be participating in the formation of intermolecular dimers by disulfide bridges. In order to obtain more stable recombinant proteins, this cysteine residue was replaced by serine (similar structural) or valine (presents in other FABPs) by site-directed mutagenesis. The obtained mutant proteins (Sm14-M2S62 and Sm14-M20V62) were not so more thermostable than the wild type Sm14-M20 protein; however, they reached approximately 100% of renaturation after the heating to 80° C., different from the wild type forms of the Sm14 protein. Moreover, after storage for 2 months at 4° C., the Sm14-M20S62 and Sm14-M20V62 mutant proteins presented a lower loss of β-structure than the wild type forms that have shown formation with random structure, as demonstrated by the circular dichroism analysis, supporting the success of mutations.

According to the present invention, mutant proteins present the following sequences.

```
SEQ ID NO:3 (M20V62)
Met Ser Ser Phe Leu Gly Lys Tpr Lys Leu Ser Glu Ser His Asn Phe Asp Ala
1               5                   10                  15

Val Met Ser Lys Leu Gly Val Ser Tpr Ala Thr Arg Gln Ile Gly Asn Thr Val
    20                  25                  30                  35

Thr Pro Thr Val Thr Phe Thr Met Asp Gly Asp Lys Met Thr Met Leu Thr Glu
            40                  45                  50

Ser Thr Phe Lys Asn Leu Ser Val Thr Phe Lys Phe Gly Glu Glu Phe Asp Glu
55                      60                  65                  70

Lys Thr Ser Asp Gly Arg Asn Val Lys Ser Val Val Glu Lys Asn Ser Glu Ser
            75                  80                  85                  90

Lys Leu thr Gln Thr Gln Val Asp Pro Lys Asn Thr Thr Val Ile Val Arg Glu
                95                  100                 105

Val Asp Gly Asp Thr Met Lys Thr Thr Val Thr Val Gly Asp Val Thr Ala Ile
    110                 115                 120                 125

Arg Asn Tyr Lys Arg Leu Ser
            130

SEQ ID NO:4 (A20C62)
Met Ser Ser Phe Leu Gly Lys Tpr Lys Leu Ser Glu Ser His Asn Phe Asp Ala
1               5                   10                  15

Val Ala Ser Lys Leu Gly Val Ser Tpr Ala Thr Arg Gln Ile Gly Asn Thr Val
    20                  25                  30                  35

Thr Pro Thr Val Thr Phe Thr Met Asp Gly Asp Lys Met Thr Met Leu Thr Glu
            40                  45                  50

Ser Thr Phe Lys Asn Leu Ser Cys Thr Phe Lys Phe Gly Glu Glu Phe Asp Glu
55                      60                  65                  70

Lys Thr Ser Asp Gly Arg Asn Val Lys Ser Val Val Glu Lys Asn Ser Glu Ser
            75                  80                  85                  90

Lys Leu thr Gln Thr Gln Val Asp Pro Lys Asn Thr Thr Val Ile Val Arg Glu
                95                  100                 105

Val Asp Gly Asp Thr Met Lys Thr Thr Val Thr Val Gly Asp Val Thr Ala Ile
    110                 115                 120                 125

Arg Asn Tyr Lys Arg Leu Ser
            130
```

SEQ ID NO:5 (T20C62)

```
Met Ser Ser Phe Leu Gly Lys Tpr Lys Leu Ser Glu Ser His Asn Phe Asp Ala
1               5                   10                  15

Val Thr Ser Lys Leu Gly Val Ser Tpr Ala Thr Arg Gln Ile Gly Asn Thr Val
        20                  25                  30                  35

Thr Pro Thr Val Thr Phe Thr Met Asp Gly Asp Lys Met Thr Met Leu Thr Glu
                40                  45                  50

Ser Thr Phe Lys Asn Leu Ser Cys Thr Phe Lys Phe Gly Glu Glu Phe Asp Glu
55                  60                  65                  70

Lys Thr Ser Asp Gly Arg Asn Val Lys Ser Val Val Glu Lys Asn Ser Glu Ser
            75                  80                  85                  90

Lys Leu thr Gln Thr Gln Val Asp Pro Lys Asn Thr Thr Val Ile Val Arg Glu
                    95                  100                 105

Val Asp Gly Asp Thr Met Lys Thr Thr Val Thr Gly Asp Val Thr Ala Ile
                110                 115                 120                 125

Arg Asn Tyr Lys Arg Leu Ser
            130
```

---

The invention claimed is:

1. Sm14 recombinant protein comprising SEQ ID NO: 2.
2. Sm14 recombinant protein comprising SEQ ID NO: 3.
3. Sm14 recombinant protein comprising SEQ ID NO: 4.
4. Sm14 recombinant protein comprising SEQ ID NO: 5.
5. Diagnosis kit comprising at least one Sm14 recombinant protein comprising at least one of SEQ ID NO: 2, SEQ ID NO:3, SEQ ID NO:4, and SEQ ID NO:5.
6. The diagnosis kit, in accordance with claim 5, wherein the kit further comprises an acceptable veterinary and/or pharmaceutical vehicle.